United States Patent
Adler et al.

(10) Patent No.: US 12,016,794 B2
(45) Date of Patent: Jun. 25, 2024

(54) PHOTOACTIVATION SYSTEMS AND METHODS FOR CORNEAL CROSS-LINKING TREATMENTS

(71) Applicant: Avedro, Inc., Waltham, MA (US)

(72) Inventors: Desmond C. Adler, Bedford, MA (US); David Usher, Waltham, MA (US); Alex Yildizyan, Waltham, MA (US)

(73) Assignee: AVEDRO, INC., Waltham, MA (US)

( * ) Notice: Subject to any disclaimer, the term of this patent is extended or adjusted under 35 U.S.C. 154(b) by 959 days.

(21) Appl. No.: 16/597,811

(22) Filed: Oct. 9, 2019

(65) Prior Publication Data
US 2020/0107953 A1 Apr. 9, 2020

Related U.S. Application Data

(60) Provisional application No. 62/810,497, filed on Feb. 26, 2019, provisional application No. 62/743,338, filed on Oct. 9, 2018.

(51) Int. Cl.
*A61F 9/00* (2006.01)
*A61N 5/06* (2006.01)
*A61N 5/067* (2006.01)

(52) U.S. Cl.
CPC .......... *A61F 9/0008* (2013.01); *A61N 5/062* (2013.01); *A61N 2005/0628* (2013.01);
(Continued)

(58) Field of Classification Search
CPC .......... A61F 9/0008; A61F 2009/00844; A61F 2009/00897; A61F 2009/00872;
(Continued)

(56) References Cited

U.S. PATENT DOCUMENTS 4,034,750 A  7/1977 Seiderman
4,665,913 A  5/1987 L'Esperance, Jr.
(Continued)

FOREIGN PATENT DOCUMENTS

DE  102008046834  3/2010
EP  1561440  8/2005
(Continued)

OTHER PUBLICATIONS

Theo G. Seiler, Isaak Fischinger, Tobias Koller, Daniel Zapp, Beatrice E. Frueh, Theo Seiler, Customized Corneal Cross-linking: One-Year Results, American Journal of Ophthalmology, vol. 166, 2016 pp. 14-21 ISSN 0002-9394, https://doi.org/10.1016/j.ajo.2016.02.029. (Year: 2016).*

(Continued)

*Primary Examiner* — Brian T Gedeon
*Assistant Examiner* — Joshua Andrew Schum-Houck
(74) *Attorney, Agent, or Firm* — K&L Gates LLP

(57) ABSTRACT

A system for treating an eye includes a light source configured to provide photoactivating light that photoactivates a cross-linking agent applied to a cornea. The system includes one or more optical elements configured to receive the photoactivating light and produce a beam that defines a spot of the photoactivating light. The system includes a scanning system configured to receive the beam of the photoactivating light and to scan the spot of the photoactivating light along a first axis and a second axis to form a scan pattern on the cornea to generate cross-linking activity.

19 Claims, 18 Drawing Sheets

(52) U.S. Cl.
CPC .............. *A61N 2005/063* (2013.01); *A61N 2005/0652* (2013.01); *A61N 2005/0661* (2013.01); *A61N 2005/0664* (2013.01); *A61N 5/067* (2021.08)

(58) Field of Classification Search
CPC ......... A61F 9/008; A61N 5/062; A61N 5/067; A61N 2005/0628; A61N 2005/063; A61N 2005/0652; A61N 2005/0661; A61N 2005/0664
See application file for complete search history.

(56) References Cited

U.S. PATENT DOCUMENTS

| | | |
|---|---|---|
| 4,712,543 A | 12/1987 | Baron |
| 4,764,007 A | 8/1988 | Task |
| 4,891,043 A | 1/1990 | Zelmer et al. |
| 4,969,912 A | 11/1990 | Kelman et al. |
| 4,994,058 A | 2/1991 | Raven et al. |
| 5,019,074 A | 5/1991 | Muller |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,624,437 A | 4/1997 | Freeman et al. |
| 5,779,696 A | 7/1998 | Berry et al. |
| 5,786,893 A | 7/1998 | Fink et al. |
| 5,891,131 A | 4/1999 | Rajan et al. |
| 5,910,110 A | 6/1999 | Bastable |
| 6,033,396 A | 3/2000 | Huang et al. |
| 6,139,876 A | 10/2000 | Kolta |
| 6,161,544 A | 12/2000 | DeVore et al. |
| 6,188,500 B1 | 2/2001 | Rudeen et al. |
| 6,218,360 B1 | 4/2001 | Cintron et al. |
| 6,270,221 B1 | 8/2001 | Liang et al. |
| 6,280,436 B1 | 8/2001 | Freeman et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,394,999 B1 | 5/2002 | Williams et al. |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,617,963 B1 | 9/2003 | Watters et al. |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,331,350 B2 | 2/2008 | Kochevar et al. |
| 7,402,562 B2 | 7/2008 | DeWoolfson et al. |
| 7,731,362 B2 | 6/2010 | Gerlach |
| 7,753,943 B2 | 7/2010 | Strong |
| 7,898,656 B2 | 3/2011 | Yun et al. |
| 7,935,058 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 8,870,934 B2 | 10/2014 | Muller et al. |
| 2001/0055095 A1 | 12/2001 | D'Souza et al. |
| 2002/0013577 A1 | 1/2002 | Frey et al. |
| 2002/0159618 A1 | 10/2002 | Freeman et al. |
| 2002/0164379 A1 | 11/2002 | Nishihara et al. |
| 2003/0175259 A1 | 9/2003 | Karageozian et al. |
| 2003/0189689 A1 | 10/2003 | Rathjen |
| 2003/0231285 A1 | 12/2003 | Ferguson |
| 2004/0002694 A1 | 1/2004 | Pawlowski et al. |
| 2004/0093046 A1 | 5/2004 | Sand |
| 2004/0199079 A1 | 10/2004 | Chuck et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0195076 A1 | 8/2006 | Blumenkranz et al. |
| 2006/0276777 A1 | 12/2006 | Coroneo |
| 2007/0024860 A1 | 2/2007 | Tobiason et al. |
| 2007/0048340 A1 | 3/2007 | Bran et al. |
| 2007/0123845 A1 | 5/2007 | Lubatschowski |
| 2007/0135805 A1 | 6/2007 | Peyman |
| 2007/0142828 A1 | 6/2007 | Peyman |
| 2007/0178714 A1 | 8/2007 | Gu et al. |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027418 A1* | 1/2008 | Berry ...................... A61F 9/008 606/5 |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0116096 A1 | 5/2009 | Zalevsky et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0234335 A1 | 9/2009 | Yee |
| 2009/0275929 A1 | 11/2009 | Zickler |
| 2010/0028407 A1 | 2/2010 | Del Priore et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0204584 A1 | 8/2010 | Ornberg et al. |
| 2010/0210996 A1 | 8/2010 | Peyman |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | Eugene et al. |
| 2011/0237999 A1 | 9/2011 | Muller et al. |
| 2011/0264082 A1 | 10/2011 | Mrochen |
| 2011/0288466 A1 | 11/2011 | Muller et al. |
| 2011/0301524 A1 | 12/2011 | Bueler et al. |
| 2011/0319874 A1* | 12/2011 | Mintz ................. A61F 9/00802 606/4 |
| 2012/0083772 A1 | 4/2012 | Rubinfield et al. |
| 2012/0215155 A1 | 4/2012 | Muller et al. |
| 2012/0203161 A1 | 8/2012 | Herekar |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1* | 12/2012 | Knox ................. A61F 9/00827 606/5 |
| 2013/0060187 A1 | 3/2013 | Friedman et al. |
| 2013/0085370 A1 | 4/2013 | Friedman et al. |
| 2013/0116757 A1 | 5/2013 | Russmann |
| 2014/0114232 A1* | 4/2014 | Hafezi ................. A61F 9/0079 604/20 |
| 2014/0194957 A1* | 7/2014 | Rubinfeld ............... A61F 9/013 607/90 |
| 2014/0249509 A1 | 9/2014 | Rubinfield et al. |

(56) References Cited

U.S. PATENT DOCUMENTS

| | | | | |
|---|---|---|---|---|
| 2015/0265762 A1* | 9/2015 | Friedman | ............... | A61F 9/0079 600/431 |
| 2016/0067086 A1* | 3/2016 | Tedford | ............... | A61N 5/0622 606/4 |
| 2016/0106311 A1* | 4/2016 | Smith | ................... | G01J 3/4406 351/221 |

FOREIGN PATENT DOCUMENTS

| | | |
|---|---|---|
| EP | 1790383 | 5/2007 |
| IT | MI2010A001236 | 5/2010 |
| KG | 1376 | 8/2011 |
| RU | 2086215 | 8/1997 |
| RU | 2420330 | 6/2011 |
| RU | 2456971 | 7/2012 |
| WO | 2000074648 | 12/2000 |
| WO | 2001058495 | 8/2001 |
| WO | 2005110397 | 11/2005 |
| WO | 2006012947 | 2/2006 |
| WO | 2006128038 | 11/2006 |
| WO | 2007001926 | 1/2007 |
| WO | 2007053826 | 5/2007 |
| WO | 2007120457 | 10/2007 |
| WO | 2007139927 | 12/2007 |
| WO | 2007143111 | 12/2007 |
| WO | 2008000478 | 1/2008 |
| WO | 2008052081 | 5/2008 |
| WO | 2008095075 | 8/2008 |
| WO | 2009073213 | 6/2009 |
| WO | 2009114513 | 9/2009 |
| WO | 2009146151 | 12/2009 |
| WO | 2010011119 | 1/2010 |
| WO | 2010015255 | 2/2010 |
| WO | 2010023705 | 3/2010 |
| WO | 2010093908 | 8/2010 |
| WO | 2011019940 | 2/2011 |
| WO | 2011116306 | 9/2011 |
| WO | 2012004726 | 1/2012 |
| WO | 2012149570 | 11/2012 |
| WO | 2012174453 | 12/2012 |
| WO | 2013148713 | 10/2013 |
| WO | 2013148895 | 10/2013 |
| WO | 2013148896 | 10/2013 |
| WO | 2013149075 | 10/2013 |
| WO | 201402736 | 12/2014 |
| WO | 2016069628 A1 | 5/2016 |

OTHER PUBLICATIONS

Rocha K., et al., "Comparative Study of Riboflavin-UVA Crosslinking and "Flash-linking" Using Surface Wave Elastometry," Journal of Refractive Surgery, vol. 24 Issue 7, pp. S748-S751; Sep. 2008 (4 pages).
Rolandi et al. Correlation of Collagen-Linked Fluorescence and Tendon Fiber Breaking Time. Gerontology 1991;27 :240-243 (4 pages).
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Spoerl E. et al., "Safety of UVA-Riboflavin Cross-Linking of the Cornea," Cornea, vol. 26, No. 4, pp. 385-389; May 2007 (5 pages).
Spoerl E., et al., "Artificial Stiffening of the Cornea by Induction of Intrastromal Cross-links," Oer Ophthalmologe, vol. 94, No. 12, pp. 902-906; Dec. 1997 (5 pages).
Spoerl E., et al., "Induction of Cross-links in Corneal Tissue," Experimental Eye Research, vol. 66, Issue 1, pp. 97-103; Jan. 1998 (7 pages).
Spoerl E., et al., "Techniques for Stiffening the Cornea," Journal of Refractive Surgery, vol. 15, Issue 6, pp. 711-713; Nov.-Dec. 1999 (4 pages).

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thorton, I. et al., "Biomechancial Effects of Intraocular Pressure Elevation on Optic Berve/Lamina Cribrosa before and after Peripapillary Scleral Collagen Cross-Linking." Invest. Ophthalmol. Vis. Sci., Mar. 2009, 50(3): pp. 1227-1233.
UV-X: Radiation System for Treatment of Keratokonus, PESCHKE Meditrade GmbH; retrieved from http://www.peschkemed.ch/ on Sep. 27, 2011 (1 page) (date unknown, prior to Sep. 16, 2008).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).
Wollensak G., "Crosslinking Treatment of Progressive Keratoconus: New Hope," Current Opinion in Ophthalmology, vol. 17(4), pp. 356-360; Aug. 2006 (5 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).
Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Wong, J. et al., "Post-Lasik ectasia: PRK following previous stablization and effective management with Riboflavin I ultraviolet A-induced collagen cross-linking," Association for Research in Vision and Ophthalmology, 2006 (1 page).
Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970).
Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 5, 2011 (pp. 13011-13022).
International Patent Application No. PCT/US2019/055482, International Search Report, dated Jan. 26, 2020 (2 pages).
International Patent Application No. PCT/US2019/055482, Written Opinion of the ISA, dated Jan. 26, 2020 (5 pages).
Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).
Averianova, O. S., "Nastoyaschee I buduschee kross-linkage." Mir Ofalmologii, 2010, [online] [retrieved on Feb. 13, 2014] Retrieved from the internet: http:/ /miroft.org.ualpublications/.html.
Baier J. et al., "Singlet Oxygen Generation by UVA Light Exposure of Endogenous Photosensitizers," Biophysical Journal, vol. 91(4), pp. 1452-1459; Aug. 15, 2006 (8 pages).

(56) References Cited

OTHER PUBLICATIONS

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).
Barbarino, S. et al., "Post-LASIK ectasia: Stabilization and Effective Managmeent with Riboflavin / ultraviolet A-induced collagen cross-linking," Association for Research in Vision and Ophthalmology, 2006 (1 page).
Bruel, A., "Changes in Biomechanical Properties, Composition of Collagen and Elastin, and Advanced Glycation Endproducts of the Rat Aorta in Relation to Age," Atherosclerosis 127, Mar. 14, 1996 (11 pages).
Chace, K.V. et al., Abstract for "The role of nonenzymatic glycosylation, transition metals, and free radicals in the formation of collagen aggregates", Arch Biochem Biophys., Aug. 1, 1991, 288(2) pp. 473-480 (1 page).
Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).
Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008 (10 pages).
Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).
Coskenseven E. et al., "Comparative Study of Corneal Collagen Cross-linking With Riboflaving and UVA Irradiation in Patients With Keratoconus," Journal of Refractive Surgery, vol. 25, issue 4, pp. 371-376; Apr. 2009 (6 pages).
Erskine H., "Avedro Becomes Sponsor of US FDA Clinical Trials of Corneal Collagen Crosslinking," Press Release, Mar. 16, 2010 (1 page).
Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).
Friedman, M. et al. "Advanced Corneal Cross-Linking System with Fluorescence Dosimetry", Journal of Ophthalmology, vol. 2012, Article ID 303459, dated May 7, 2012 (6 pages).
Gibson, Q. et al., "The Oxidation of Reduced Flavin Mononucleotide by Molecular Oxygen," Biochem. J. (1962) 83, 368-377 (10 pages).
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009 (11 pages).
Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009 (4 pages).
Hitzenberger et al., "Birefringence Properties of the Human Cornea Measured With Polarization Sensitive Optical Coherence Tomography," Bull. Soc. Beige Ophtalmol., 302, 153-168, 2006.
Holmstrom, B. et al., "Riboflavin as an Electron Donor in Photochemical Reactions," 1867-1871, Nov. 29, 1960 (5 pages).
IMEX, "KXL System: Crosslinking Para Cirugia Corneal Bibliografia Cientifica," Product Literature, Nov. 23, 2010 (24 pages).
Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," Investigative Opthalmology & Visual Science, vol. 51, No. 8, pp. 3929-3934; Aug. 2010 (6 pages).
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UV A-induced collagen cross-linking followed by a limited topo-guided surface excimer ablation," American Academy of Ophthalmology, 2006 (25 pages).
Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).
Kissner Anja, et al., "Pharmacological Modification of the Epithelial Permeability by Benzalkonium Chloride in UVNRiboflavin Corneal Collagen Cross-Linking," Current Eye Research 35(8), pp. 715-721; Mar. 2010 (7 pages).
Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, val. 224, No. 9, pp. 700-706; Sep. 2007 (7 pages).
Koller, T. et al., "Complication and failure rates after corneal crosslinking," Journal Cataract and refractive surgery, vol. 35, No. 8, Aug. 2009, pp. 1358-1362.
Kornilovsky, I. M. "Novye neinvazivnye tekhnologii lazernoy modifikatsii optiko-refraksionnykk struktur glaza. Refraktsionnaya khirurgiya l oftalmologiya." vol. 9, No. 3, 2006 (pts. 17-26).
Krueger Ronald R., "Rapid VS Standard Collagen CXL with Equivalent Energy Dosing," presentation slides, (26 pages); available at http://www.slideshare.net/logen/krueger-kerekar-rapid-cross-linking (date unknown, prior to Nov. 9, 2009).
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Marzouky, et al., Tensioactive-mediated Transepithelial Corneal Cross-linking—First Laboratory Report, European Ophthalmic Review, 2009, 3(2), pp. 67-70.
Massey, V., "Activation of Molecular Oxygen by Flavins and Flavoproteins," The Journal of Biological Chemistry vol. 269, No. 36, Issue of Sep. 9, pp. 22459-22462, 1994 (4 pages).
Meek, K.M. et al. "The Cornea and Sclera", Collagen: Structure and Mechanics, Chapter 13, pp. 359-396, 2008 (38 pages).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
Pinelli R., et al., "C3-Riboflaving Treatments: Where Did We Come From? Where Are We Now?" Cataract & Refractive Surgery Today Europe, Summer 2007, pp. 36-46; Jun. 2007 (10 pages).
Pinelli, R. "Corneal Cross-Linking with Riboflavin: Entering a New Era in Ophthalmology." Ophthalmology Times Europe. vol. 2, No. 7, Sep. 1, 2006 (3 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Ponce C., et al., "Central and Peripheral Corneal Thickness Measured with Optical Coherence Tomography, Scheimpflug Imaging, and Ultrasound Pachymetry in Normal, Keratoconus-suspect and

(56) References Cited

OTHER PUBLICATIONS

Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurement and Intrepretation of Brillouin Scattering in the Lens of the Eye," The Royal Society, Abstract only, published 2013 [available online at http://rspb.royalsocietypublishing.org/content/214/11971449.short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

\* cited by examiner

514a

514b

PHOTOACTIVATION SYSTEMS AND METHODS FOR CORNEAL CROSS-LINKING TREATMENTS

CROSS-REFERENCE TO RELATED APPLICATIONS

This application claims the benefit of, and priority to, U.S. Provisional Patent Application No. 62/743,338, filed Oct. 9, 2018, and U.S. Provisional Patent Application No. 62/810,497, filed Feb. 26, 2019, the contents of these applications being incorporated entirely herein by reference.

BACKGROUND

Field

The present disclosure pertains to systems and methods for eye treatments, and more particularly, to systems and methods for photoactivating a cross-linking agent in corneal cross-linking treatments.

Description of Related Art

Corneal ectatic disorders, or corneal ectasia, are a group of uncommon, noninflammatory, eye disorders characterised by bilateral thinning of the central, paracentral, or peripheral cornea.

For instance, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

For instance, a complication known as post-LASIK ectasia may occur due to the thinning and weakening of the cornea caused by Laser-Assisted in situ Keratomileusis surgery (LASIK) surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

SUMMARY

Embodiments include systems and methods for photoactivating a cross-linking agent in corneal cross-linking treatments.

According to an example embodiment, a system for treating an eye includes a light source configured to provide photoactivating light that photoactivates a cross-linking agent applied to a cornea. The system includes one or more optical elements configured to receive the photoactivating light and produce a beam that defines a spot of the photoactivating light. The system includes a scanning system configured to receive the beam of the photoactivating light and to scan the spot of the photoactivating light along a first axis and a second axis to form a scan pattern on the cornea to generate cross-linking activity.

According to another example embodiment, a system for treating an eye includes a light source configured to provide photoactivating light that photoactivates a cross-linking agent applied to a cornea. The system includes one or more optical elements configured to receive the photoactivating light and produce a pattern of photoactivating light. The system includes a fiber-optic element configured to receive the pattern of photoactivating light from the one or more optical elements and transmit the pattern of photoactivating light to the cornea to generate cross-linking activity.

Figure 1:
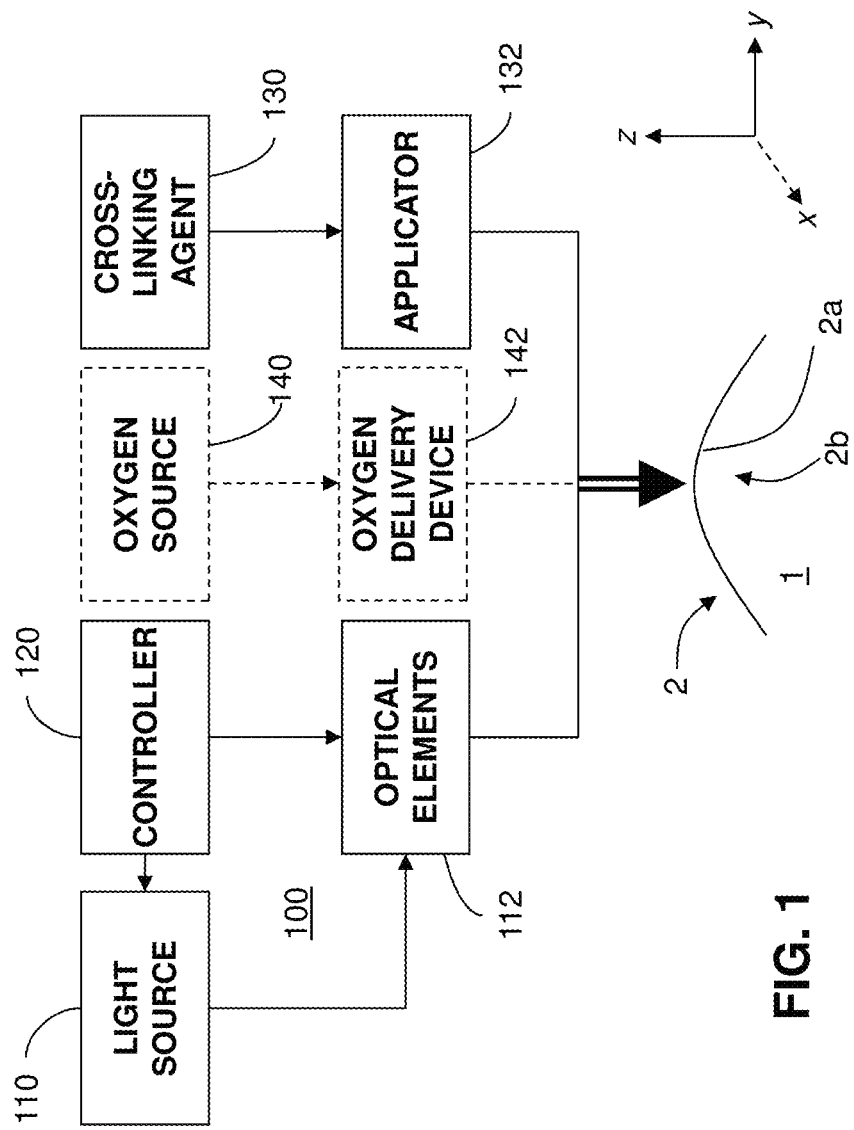
FIG. 1 illustrates an example system that delivers a cross-linking agent and photoactivating light to a cornea of an eye in order to generate cross-linking of corneal collagen, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent is described in U.S. patent application Ser. No. 10/342,697, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address corneal ectatic disorders, such as keratoconus or post-LASIK ectasia. Additionally, the application of riboflavin and the photoactivating light may to allow for various amounts of refractive correction, which for instance, may involve combinations of myopia, hyperopia, astigmatism, irregular astigmatism, presbyopia and complex corneal refractive surface corrections due to corneal ectatic disorders as well as other conditions of corneal biomechanical alteration/degeneration, etc.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photoactivating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a microelectromechanical system (MEMS) device, e.g., a digital micro-mirror device (DMD), to modulate the application of photoactivating light spatially and temporally. Using DMD technology, the photoactivating light from the light source 110 is projected in a precise spatial pattern that is created by microscopically small mirrors laid out in an array on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real time monitoring and modulation of corneal cross-linking during treatment. Aspects of a dosimetry system are described in further detail below. Additionally, pre-clinical patient information may be combined with finite element biomechanical computer modeling to create patient specific pre-treatment plans. Aspects of a treatment system employing a DMD are described further below with reference to FIGS. 2A-B.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 $mW/cm^2$ to approximately 1000 $mW/cm^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference. Embodiments may generate cross-linking activity in the cornea according to circular and/or annular patterns defined by the delivery of photoactivating light (e.g., via the DMD described above). Additionally or alternatively, embodiments may generate cross-linking activity in the cornea according to non-circular and/or non-annular patterns defined by the delivery of photoactivating light (e.g., via the DMD).

Patterns of photoactivating light can be applied (e.g., via the DMD) to the eye in separate treatment zones with different doses sequentially or continuously applied. For instance, one treatment zone can be "turned off" (i.e., delivery of the corresponding photoactivating light ceases) while another "stays on" (i.e., delivery of the corresponding photoactivating light continues). The treatment zones can be, for instance, annularly shaped about a center point of the eye. There may also be discontinuous zones where no the photoactivating light is applied (e.g., a central treatment zone surrounded by an annulus of no light surrounded by an annular treatment zone of light, etc.). The widths of the annular zones can be of different dimensions, e.g., one annular zone has a width of 1 mm and another has a width of 2 mm. Applying the photoactivating light in annular treatment zones on the periphery of the eye without a central treatment zone can result in a hyperopic correction, for instance, by causing the central region of the eye to have an increased curvature while the periphery is strengthened. In some cases, central and surrounding treatment zones can be elliptical in shape, for instance to address astigmatism, by preferentially generating cross-linking activity in regions of the cornea to correct the astigmatism. Such elliptically shaped annular treatment zones are preferentially oriented with the axis of the annular treatment zones aligned according to the orientation of the astigmatism. The elliptically shaped treatment zones can also be irregularly asymmetric (i.e., having major and minor axis that are not perpendicular and can be situated with distinct center points (centers of mass)).

Cross-linking treatments can be tuned according to one or more biomechanical properties of the eye, such as the corneal topography (i.e., shape), corneal strength (i.e., stiffness), and/or corneal thickness. Optical correction and/or strengthening of the cornea can be achieved by applying the cross-linking agent and/or photoactivating light in one or more iterations with adjustable characteristics for each iteration. Generally, a developed treatment plan can include a number of applications of the cross-linking agent, the amount and concentration of the cross-linking agent for each application, the number of applications of photoactivating light, and the timing, duration, power, energy dosage, and pattern of the photoactivating light for each application. Furthermore, the cross-linking treatments can be adapted based on feedback information relating to the biomechanical properties gathered in real time during treatment or during breaks in treatments.

The addition of oxygen also affects the amount of corneal cross-linking. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Pat. No. 9,707,126, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 5, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photoactivation. There are two photochemical kinetic pathways for riboflavin photoactivation, Type I and Type II. The reactions involved in both the Type I and Type II mechanisms and other aspects of the photochemical kinetic reactions generating cross-linking activity are described in U.S. Pat. No. 10,350,111, filed Apr. 27, 2016 and titled "Systems and Methods for Cross-Linking Treatments of an Eye," the contents of which are incorporated entirely herein by reference.

As described above, the treatment system 100 includes optical elements 112 that direct light (e.g., UV light) from a light source 110 to photoactivate the cross-linking agent 130 (e.g., riboflavin) applied to the cornea 2 and thus generate cross-linking activity. In particular, the photoactivating light can be selectively directed to regions of the cornea 2 according to a particular spatial treatment pattern. In some embodiments, a treatment system can provide an adjustable treatment pattern so that different ophthalmic conditions can be treated with the same treatment system.

Figure 2A:
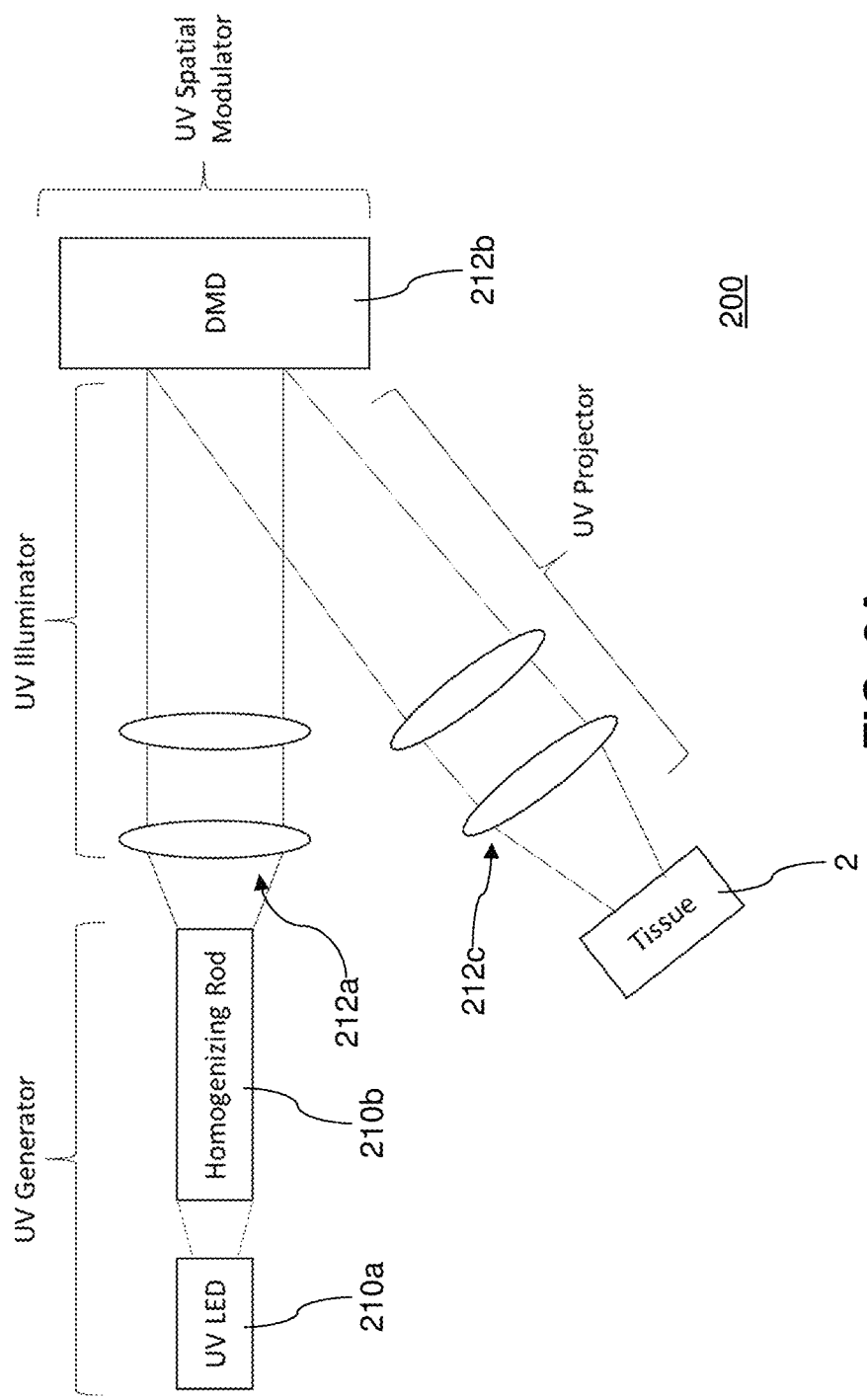
FIG. 2A illustrates an example treatment system, where ultraviolet (UV) light is generated with a light emitting diode (LED), illuminated onto a digital micro-mirror device (DMD) using a first set of free space optics, and projected onto target tissue using a second set of free space optics.

FIG. 2A illustrates an example treatment system 200 that can treat different ophthalmic conditions by providing different treatment patterns. The treatment system 200 includes a light emitting diode (LED) 210a and a homogenizing rod 210b that generate UV light. The treatment system 200 also includes a first set of free space optical elements 212a that illuminates the UV light onto a DMD 212b. The DMD 212b can spatially modulate the UV light according to a desired treatment pattern by selectively directing the UV light on a pixel-by-pixel basis to a second set of free space optical elements 212c. The second set of free space optical elements 212c then projects (i.e., focuses) the pattern of UV light from the DMD 212b as output onto the cornea 2.

As generally labelled in the Figures, "UV Generator" refers to one or more elements that generate UV light; "UV Spatial Modulator" refers to one or more elements that spatially modulate the UV light to define a UV light pattern; "UV Illuminator" refers to one or more elements that illuminate the UV Spatial Modulator with the UV light from the UV Generator; and "UV Projector" refers to one or more elements that project the UV light pattern from the UV Spatial Modulator onto target tissue. Additionally, as shown in the Figures, the depth of the cornea is measured along a z-axis and patterns of photoactivating light may be projected on transverse x-y planes.

In the treatment system 200, the UV light is manipulated and transmitted with free-space (i.e., bulk) optical elements, such as the first set of free space optical elements 212a and the second set of free space optical elements 212c. Disadvantageously, strict three-dimensional alignment must be maintained between each free space optical element to prevent distortion of the desired treatment pattern and loss of power for the UV light. Such alignment must be maintained over time against vibration and/or variations in temperature and/or humidity. Such alignment must also account for part-to-part variations between the free space optical elements. The need to maintain alignment can result in higher system complexity and/or cost and can negatively impact reliability.

Figure 2B:
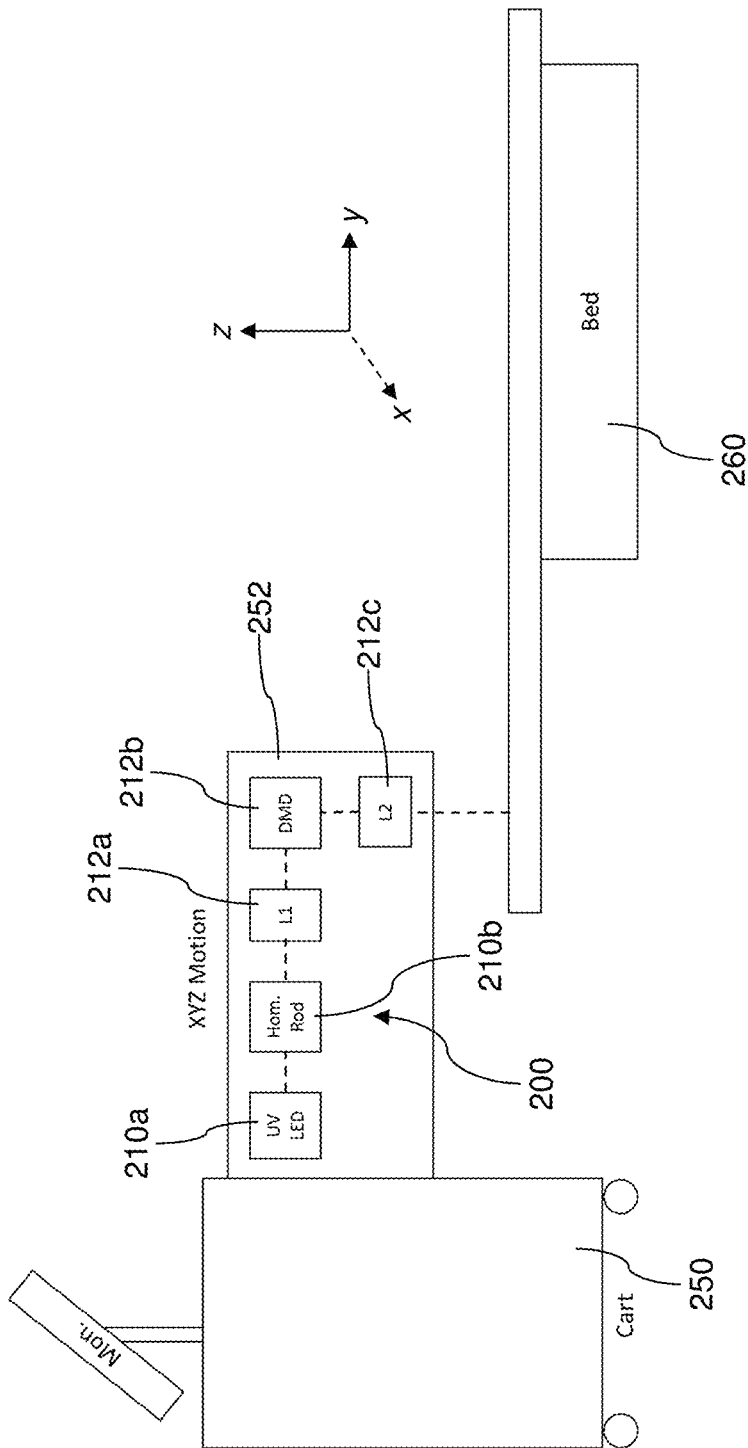
FIG. 2B illustrates an example implementation of the treatment system shown in FIG. 2A.

Additionally, to align the UV light pattern with desired regions of the cornea 2, the treatment system 200 must allow three-dimensional adjustment of the output UV light. FIG. 2B, for instance, illustrates an example implementation of the treatment system 200, where the elements 210a-b, 212a-c are assembled in combination with a cart 250, and the subject with the cornea 2 is situated on a bed 260. All optical interfaces between the elements 210a-b, 212a-c are free space (shown in FIG. 2B as dashed lines). The UV light pattern projected by the second set of free space optical elements 212c can be translated in the x-, y-, and z-directions relative to the bed 260 and the cornea 2. To allow translation of the output UV light, the assembly of the elements 210a-b, 212a-c correspondingly translates in the x-, y-, and z-directions while maintaining the necessary alignment between the elements 210a-b, 212a-c. In particular, the elements 210a-b, 212a-c may be assembled on an XYZ motion stage 252 that is movably coupled to the cart 250 and can translate the entire assembly relative to the bed 260. Use of the XYZ motion stage 252, however, may require a larger footprint and may involve more complexity for the treatment system 200 as compared to other treatment systems described below.

According to aspects of the present disclosure, optical elements of a treatment system can employ fiber-optic elements to avoid some of the disadvantages of the treatment system 200. The use of fiber-optic elements can eliminate the need for free space optical elements as well as opto-mechanical mounts in a treatment system. Advantageously, the use of fiber-optics can reduce the size and footprint of a treatment system, reduce design and manufacturing complexity and cost, and enhance reliability.

Figure 3A:
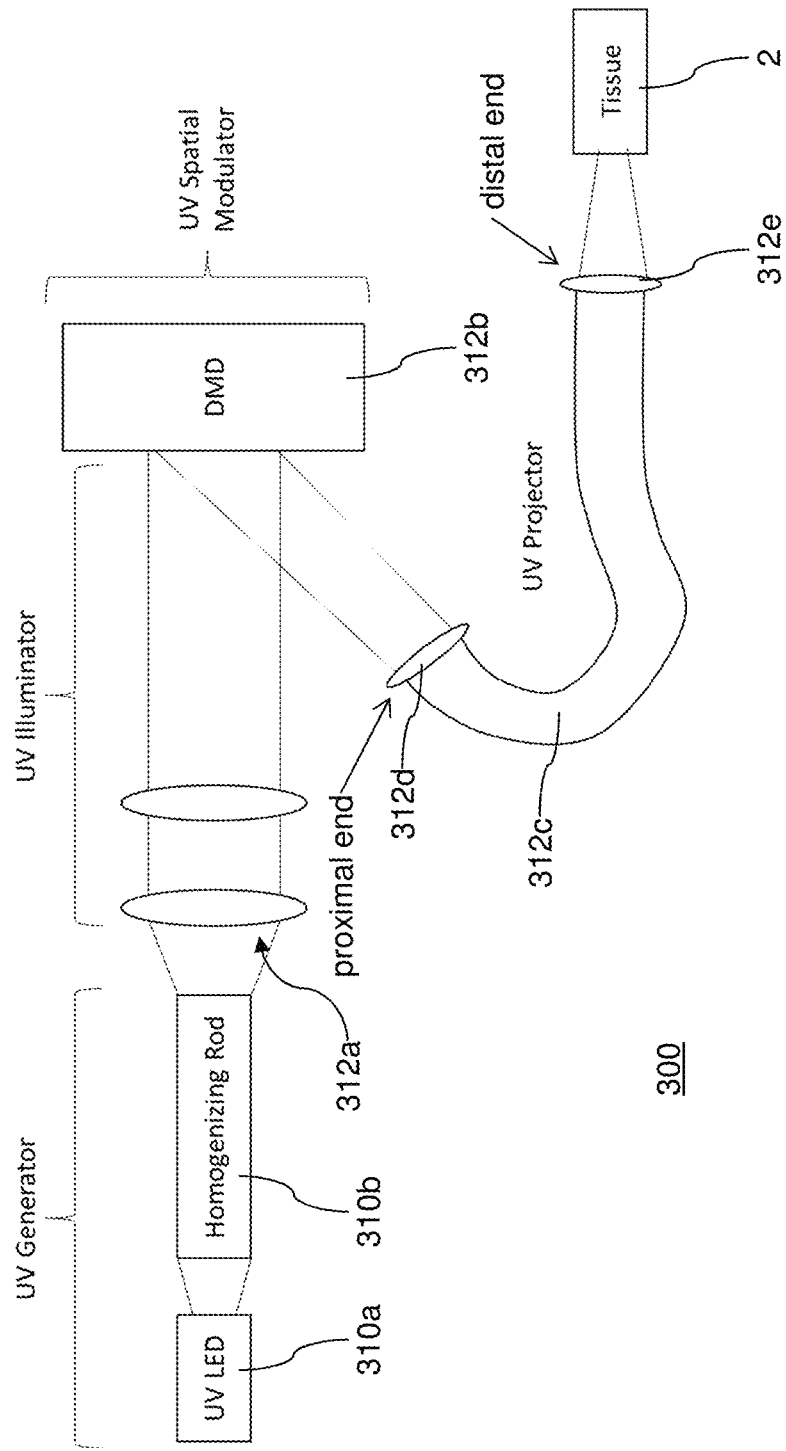
FIG. 3A illustrates an example treatment system, where UV light is generated with a LED, illuminated onto a DMD using a set of free space optics, and projected onto target tissue using a flexible coherent fiber bundle, according to aspects of the present disclosure.

FIG. 3A illustrates an example treatment system 300 employing fiber-optic elements. Similar to the treatment system 200 described above, the treatment system 300 includes a LED 310a and a homogenizing rod 310b to generate UV light. The treatment system 300 also includes a first set of free space optical elements 312a that illuminates the UV light onto a DMD 312b, which produces a desired UV light pattern. In contrast to the treatment system 200, however, the UV light pattern from the DMD 312b is not directed to a second set of free-space optical components. Instead, the UV light pattern is directed to a flexible, coherent fiber bundle 312c. The coherent fiber bundle 312c can then be flexibly routed to extend to a position where it can project the UV light pattern onto the cornea 2. The coherent fiber bundle 312c is assembled from thousands of individual fibers, where 1:1 relative spatial orientation is maintained between a proximal end and a distal end of the coherent fiber bundle 312c. (As used herein, "proximal" generally refers to an upstream location that is closer to the light source, while "distal" generally refers to a downstream location that is closer to the target tissue.) The coherent fiber bundle 312c, for instance, may have between 10,000 and 100,000 or more individual fibers, which are often referred to as pixels.

The coherent fiber bundle 312c may be employed with optical elements, such as lenses, which are coupled to the proximal and/or distal end of the coherent fiber bundle 312c to assist in receiving and transmitting the UV light pattern. As shown in FIG. 3A, a first lens 312d may be coupled to the proximal end of the coherent fiber bundle 312c to receive the UV light pattern from the DMD 312b. Meanwhile, a second lens 312e may be coupled to the distal end of the coherent fiber bundle 312c to provide a desired size for the UV light pattern at a desired working distance from the treatment system 300, where the cornea 2 is positioned.

Figure 3B:
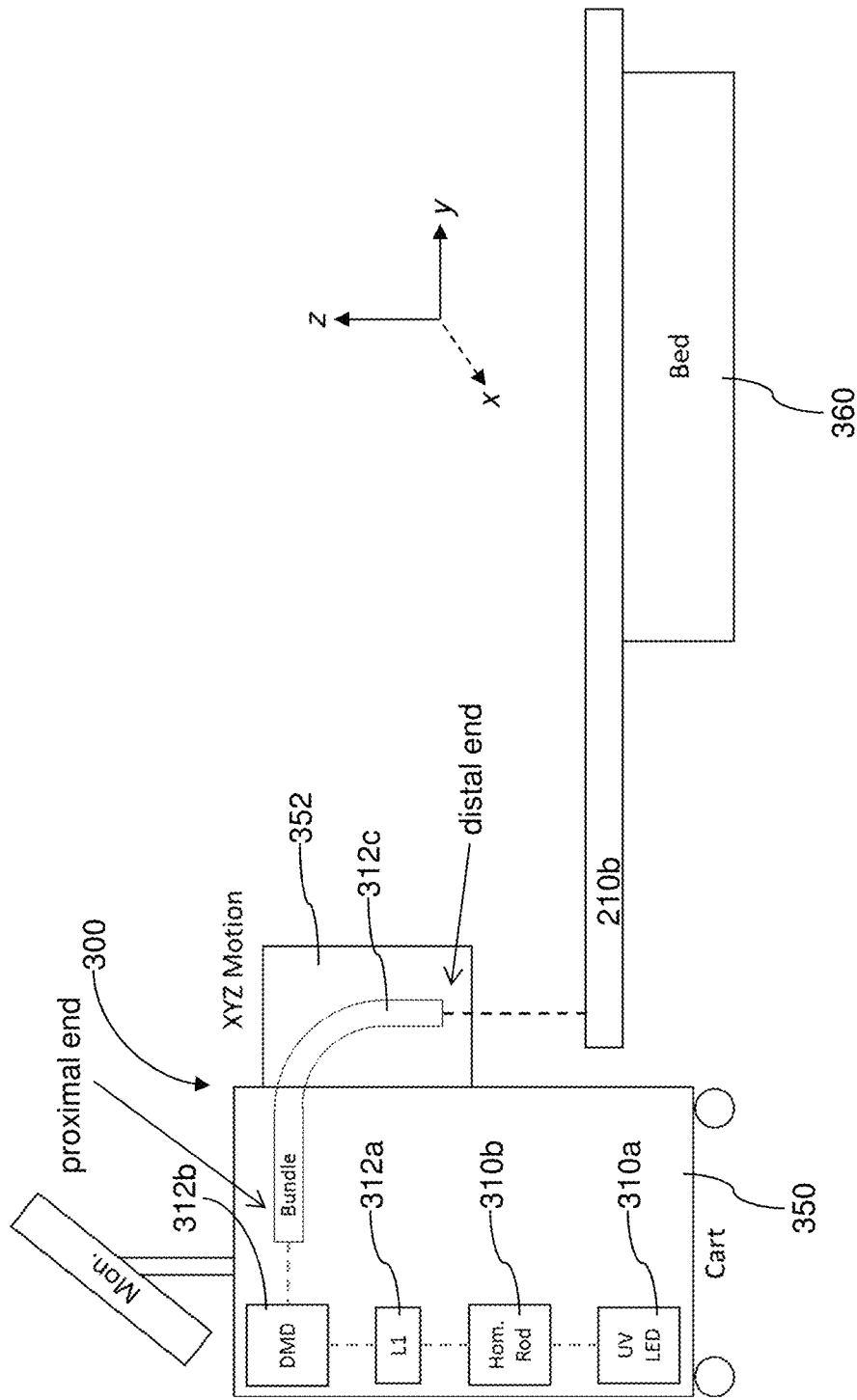
FIG. 3B illustrates an example implementation of the treatment system shown in FIG. 3A, according to aspects of the present disclosure.

FIG. 3B illustrates an example implementation of the treatment system 300, where the elements 310a-b, 312a-c are assembled in combination with a cart 350, and the subject with the cornea 2 is situated on a bed 360. When compared with FIG. 2B, FIG. 3B shows how the use of the coherent fiber bundle 312c can improve the implementation of a treatment system. The optical interfaces between the elements 310a-b, 312a-c are free space (shown as dashed lines in FIG. 3B). An XYZ motion stage 352 is movably coupled to the cart 350 and allows the UV light pattern projected from treatment system 300 to be translated in the x-, y-, and z-directions relative to the bed 360 and the cornea 2. Because the coherent fiber bundle 312c is flexible, the distal end can be coupled to the XYZ motion stage 352 and moved in the x-, y-, and z-directions while the proximal end remains in a fixed location relative to the DMD 312b. The XYZ motion stage 352 can be operated to align the distal end of the coherent fiber bundle 312c with the cornea 2 and deliver the UV light pattern to the desired regions of the cornea 2. Meanwhile, the elements 310a-b, 312a-b as well as the proximal end of the coherent fiber bundle 312c may be disposed on the cart 350. Unlike the XYZ motion stage 352, the cart 350 does not provide translation in the x-, y-, and z-directions. Accordingly, the use of the flexible coherent fiber bundle 312c allows the size, weight, and complexity of the XYZ motion stage 352 to be reduced, in contrast to the XYZ motion stage 252 shown in FIG. 2B. Additionally, the opto-mechanical challenges associated with mounting and aligning the elements 310a-b, 312a-c can be significantly reduced.

Figure 4A:
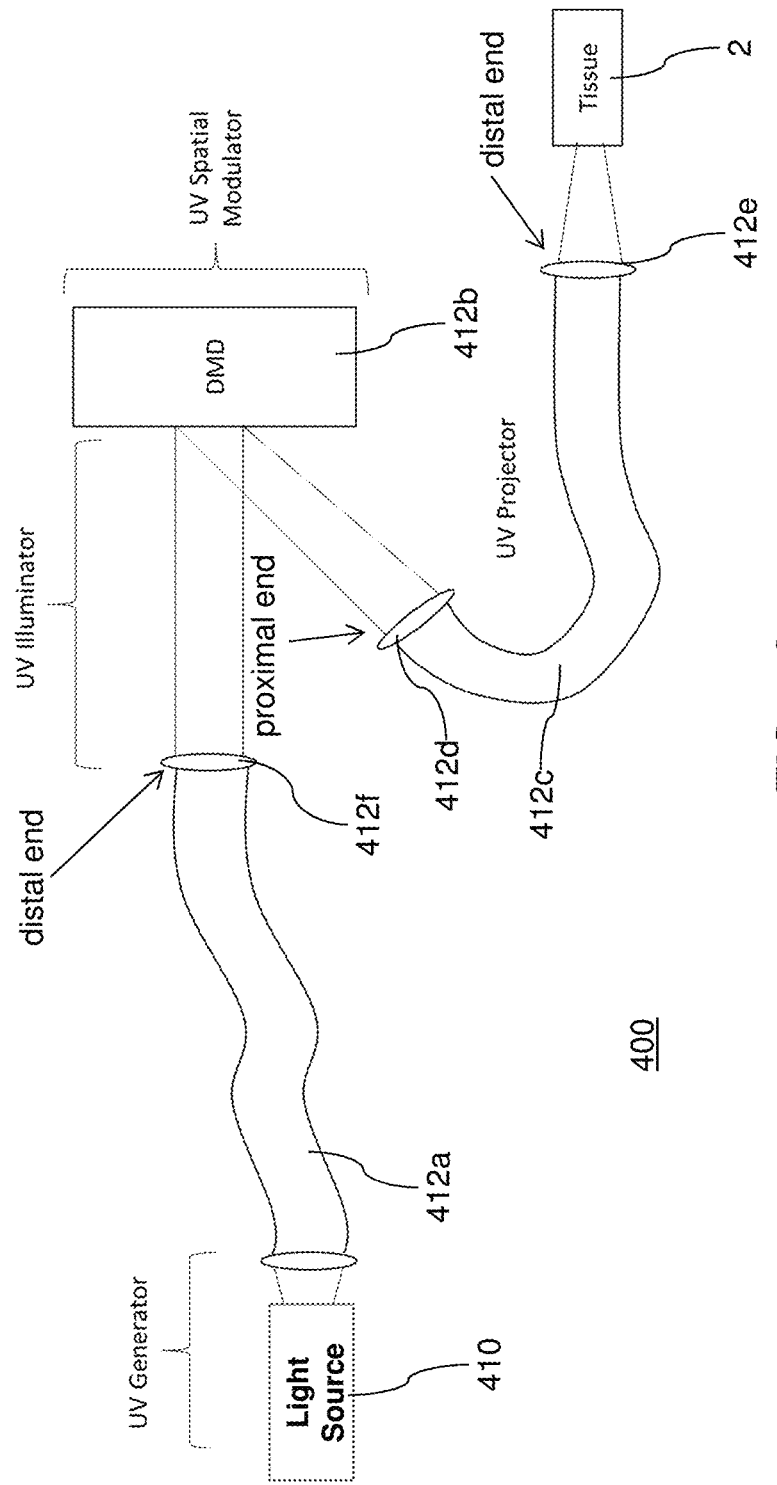
FIG. 4A illustrates another example treatment system, where UV light is generated with a LED that is fiber-coupled to a single optical fiber and illuminated onto a DMD through a lens, and a resulting UV light pattern is projected onto target tissue using a flexible coherent fiber bundle, according to aspects of the present disclosure.

FIG. 4A illustrates another example treatment system 400 employing fiber-optic elements. Like the treatment system 300 described above, the treatment system 400 includes a DMD 412b, which produces a desired UV light pattern. Additionally, a flexible, coherent fiber bundle 412c receives the UV light pattern from the DMD 412b and projects the UV light pattern onto the cornea 2. Lenses 412d, 412e may be coupled to the proximal and distal ends of the coherent fiber bundle 412c, respectively, to assist in receiving and transmitting the UV light pattern. In contrast to the treatment system 300, however, the treatment system 400 does not employ a homogenizing rod to generate UV light with a light source. The treatment system 400 also does not employ a first set of free space optical elements to illuminate the UV light onto the DMD 412b. Instead, the treatment system 400 employs a light source 410 that is fiber-coupled to the proximal end of a single flexible optical fiber 412a. The light source may be a UV LED or a UV laser source (e.g., single-mode or multi-mode). The optical fiber 412a can be flexibly routed to a location close to the DMD 412b. A lens 412f, such as a collimating lens, focusing lens, or similar optical element(s), can be placed in optical communication with a distal end of the optical fiber 412a to illuminate the UV light onto the DMD 412b. The lens 412f may be held in position with respect to the ceramic ferrule of the fiber termination, providing intrinsic centration with a simple and reliable mount. Alternatively, the lens 412f may be held in position a fixed distance away from the distal end of the optical fiber 412a, allowing for a controlled amount of beam expansion for the UV light prior to entering the lens 412f. This allows the UV light to be illuminated onto the DMD 412b as a spot with a size that can be controlled by selecting an appropriate lens 412f and distance.

The optical fiber 412a may be a multi-mode fiber to provide spatial homogenization of the UV light traveling through the optical fiber 412a, especially if the light source 410 is an LED or a multi-mode laser source. Larger core sizes around 100 µm, 1000 µm, or 2000 µm can provide greater amounts of homogenization while reducing UV intensity inside the optical fiber 412a to reduce the risk of photodegradation. If additional homogenization is required, a partially transmissive mask may be applied to the output of the optical fiber 412a. Alternatively, the DMD 412b may be used to partially attenuate portions of the UV light in order to achieve a homogenous UV light pattern. The light source 410 may also have integrated optical power control to simplify system integration. If the light source 410 is a single-mode laser source, rather than a UV LED or a multi-mode laser source, spatial homogenization may not be required and the fiber 412a may be a single-mode fiber. Various alternate strategies may be used to couple the light source 410 to the optical fiber 412a, such as provision of a lensed fiber or direct butt-coupling of the optical fiber 412a to a laser emitter.

Figure 4B:
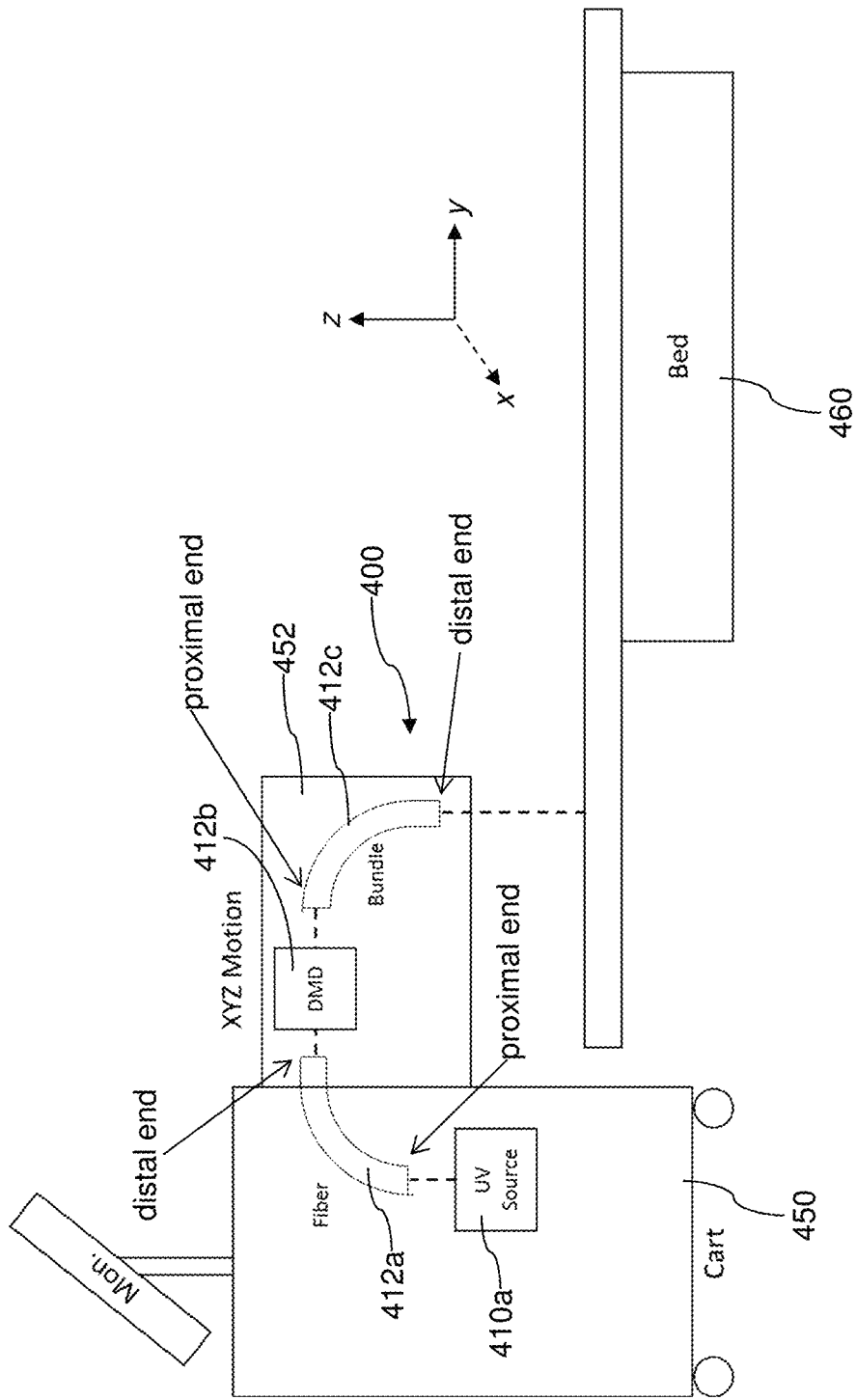
FIG. 4B illustrates an example implementation of the treatment system shown in FIG. 4A, according to aspects of the present disclosure.

FIG. 4B illustrates an example implementation of the treatment system 400, where the elements 410, 412a-d are assembled in combination with a cart 450, and the subject with the cornea 2 is situated on a bed 460. FIG. 4B shows how the use of the fiber-coupled light source 410 can improve the implementation of a treatment system. The optical interfaces between the elements 410, 412a-c are free space (shown as dashed lines in FIG. 4B). An XYZ motion stage 452 is movably coupled to the cart 450 and allows the UV light pattern projected from treatment system 400 to be translated in the x-, y-, and z-directions relative to the bed 460 and the cornea 2. The XYZ motion stage 452 can be operated to align the distal end of the coherent fiber bundle 412c with the cornea 2 and deliver the UV light pattern to the desired regions of the cornea 2. Because the optical fiber 412a is flexible, the distal end of the optical fiber 412a can be coupled to the XYZ motion stage 452 while the proximal end remains in a fixed location relative to the light source 410. Correspondingly, the DMD 412b and the coherent fiber bundle 412c are disposed on the XYZ motion stage 452, while the light source 410 is disposed on the cart 450.

Alternatively, because the coherent fiber bundle 412c is flexible, the distal end of the coherent fiber bundle 412c may be coupled to the XYZ motion stage 452, while the elements 410, 412a-b as well as the proximal end of the coherent fiber bundle 412c may be disposed on the cart 450. This alternative implementation is similar to the implementation shown in FIG. 3B.

The treatment system 400 provides greater design freedom, because the treatment system 400 includes both the flexible optical fiber 412a and the flexible coherent fiber bundle 412c. The optical fiber 412a and the coherent fiber bundle 412c allow the elements 410, 412a-d to be positioned on the cart 250 and the XYZ motion stage 452 according to different configurations. The configurations can reduce the size, weight, and complexity of the XYZ motion stage 452. Additionally, the opto-mechanical challenges associated with mounting and aligning the elements 410, 412a-c can be significantly reduced.

According to further aspects of the present disclosure, the optical elements may include a XY scanning mirror pair to form the UV light pattern. The use of the XY scanning mirror can eliminate the need for a DMD or similar spatial filter. Advantageously, by employing a XY scanning mirror, embodiments can further reduce the size of the treatment system, reduce design and manufacturing complexity and cost, and enhance reliability.

Figure 5A:
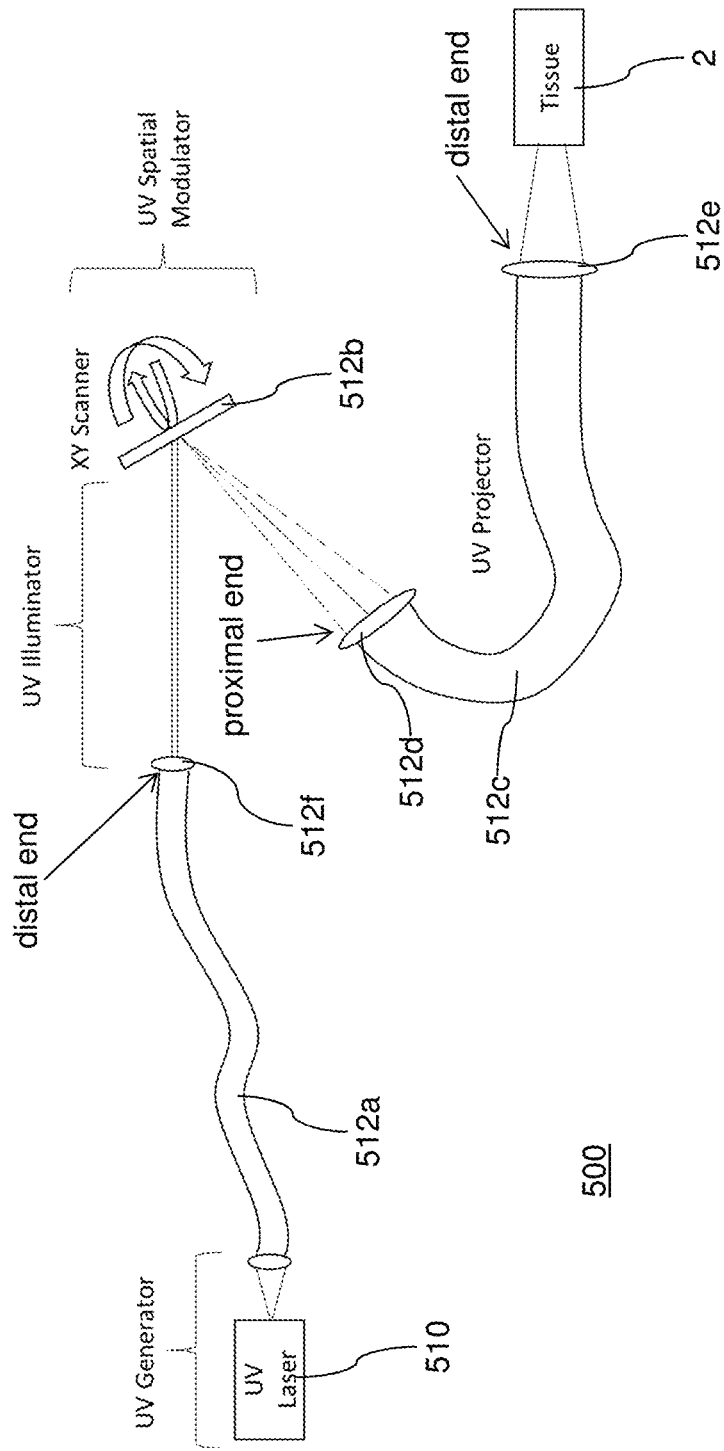
FIG. 5A illustrates yet another example treatment system, where UV light is generated with a laser source that is fiber-coupled to a single optical fiber and illuminated onto a XY scanning system, and a resulting UV light scan pattern is projected onto target tissue using a flexible coherent fiber bundle, according to aspects of the present disclosure.

FIG. 5A, for instance, illustrates an example treatment system 500 that employs an XY scanning system instead of a DMD. The treatment system 500 includes a UV laser source 510 that is fiber-coupled to a single optical fiber 512a (e.g., multi-mode or single-mode). The treatment system 500 also includes a lens 512f, such as a collimating lens, focusing lens, or similar optical element(s), disposed at or near the distal end of the optical fiber 512a. Additionally, the treatment system 500 includes a galvanometer pair 512b that acts as the XY scanning system. The UV laser travels through the optical fiber 512a and the lens 512f produces a UV light beam with a small, high-quality spot on the galvanometer pair 512b. The galvanometer pair 512b includes a first mirror that can scan the UV light beam in the x-direction and a second mirror that can scan the UV light beam in the y-direction. The treatment system 500 also includes a coherent fiber bundle 512c. The galvanometer pair 512b scans the UV light beam over the face at the proximal end of the coherent fiber bundle 512c according to a desired pattern. The coherent fiber bundle 512c then projects the UV light scan pattern to the cornea 2 according to the desired treatment pattern. Lenses 512d, 512e may be coupled to the proximal and distal ends of the coherent fiber bundle 512c, respectively, to assist in receiving and transmitting the UV light scan pattern.

Figure 5B:
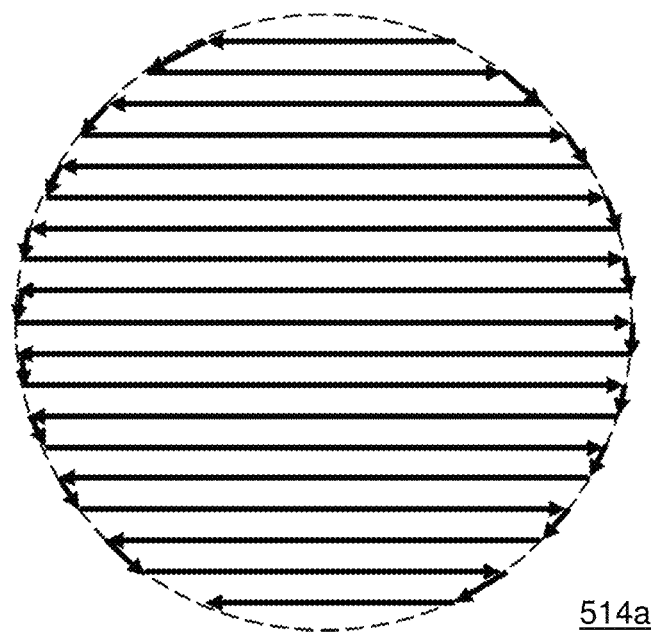
FIG. 5B illustrates an example pattern that the XY scanning system of FIG. 5A can scan over the proximal face of the coherent fiber bundle to produce a circular treatment pattern on the target tissue, according to aspects of the present disclosure.
Figure 5C:
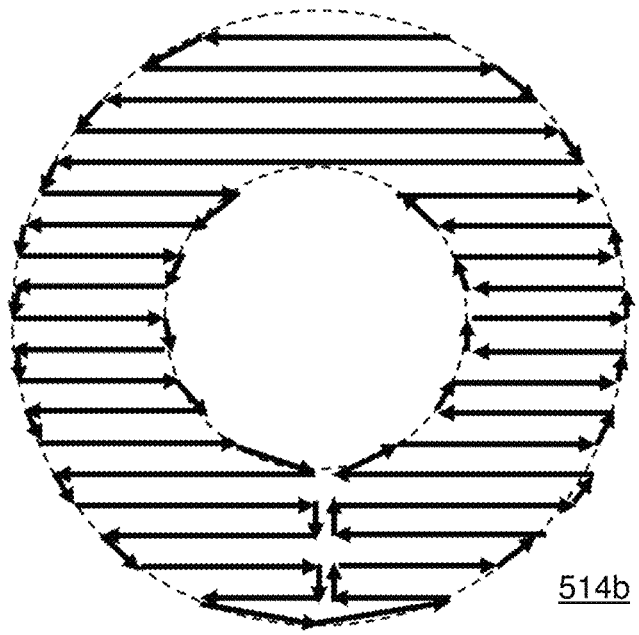
FIG. 5C illustrates an example pattern that the XY scanning system of FIG. 5A can scan over the proximal face of the coherent fiber bundle to produce an annular treatment pattern on the target tissue, according to aspects of the present disclosure.

A practitioner can determine the desired treatment pattern, which is translated into independent mirror drive waveforms that cause the first and second mirrors to scan the UV light beam in the x- and y-directions, respectively. FIG. 5B illustrates an example pattern 514a that the galvanometer pair 512b can scan over the proximal face of the coherent fiber bundle 512c to produce a circular treatment pattern on the cornea 2. FIG. 5C illustrates an example pattern 514b that the galvanometer pair 512b can scan over the proximal face of the coherent fiber bundle 512c to produce an annular treatment pattern on the cornea 2. Other scan patterns are also possible. The speed of the first and/or second mirrors of the galvanometer pair 512b can be adjusted during part of the scan in order to increase or decrease dwell time over a portion of the scan pattern, thereby adjusting the corresponding dose of UV light applied in portions of the scan pattern. Additionally, the entire scan pattern may be continuously shifted over the distal tip of the fiber bundle in the x- and y-directions in response to eye motion. In this way, the UV light pattern can be kept centered over a desired portion of the cornea 2 during the treatment, even if the eye is moving. (This continuous shift can also be provided by the DMD in the treatment systems described above).

When a coherent fiber bundle is employed to project the UV light pattern formed by a DMD or a XY scanning system, the UV light pattern is effectively sampled by the discrete fibers defining the coherent fiber bundle. If an insufficient number of fibers are used to make the coherent fiber bundle, the UV light pattern projected onto the cornea is undersampled and appears undesirably quantized. If too many fibers are used to make the coherent fiber bundle, the cost of the coherent fiber bundle is unnecessarily higher. It is therefore desirable to optimize the number of fibers in the coherent fiber bundle to achieve the desired size and resolution for the UV light pattern projected onto the cornea.

Figure 6:
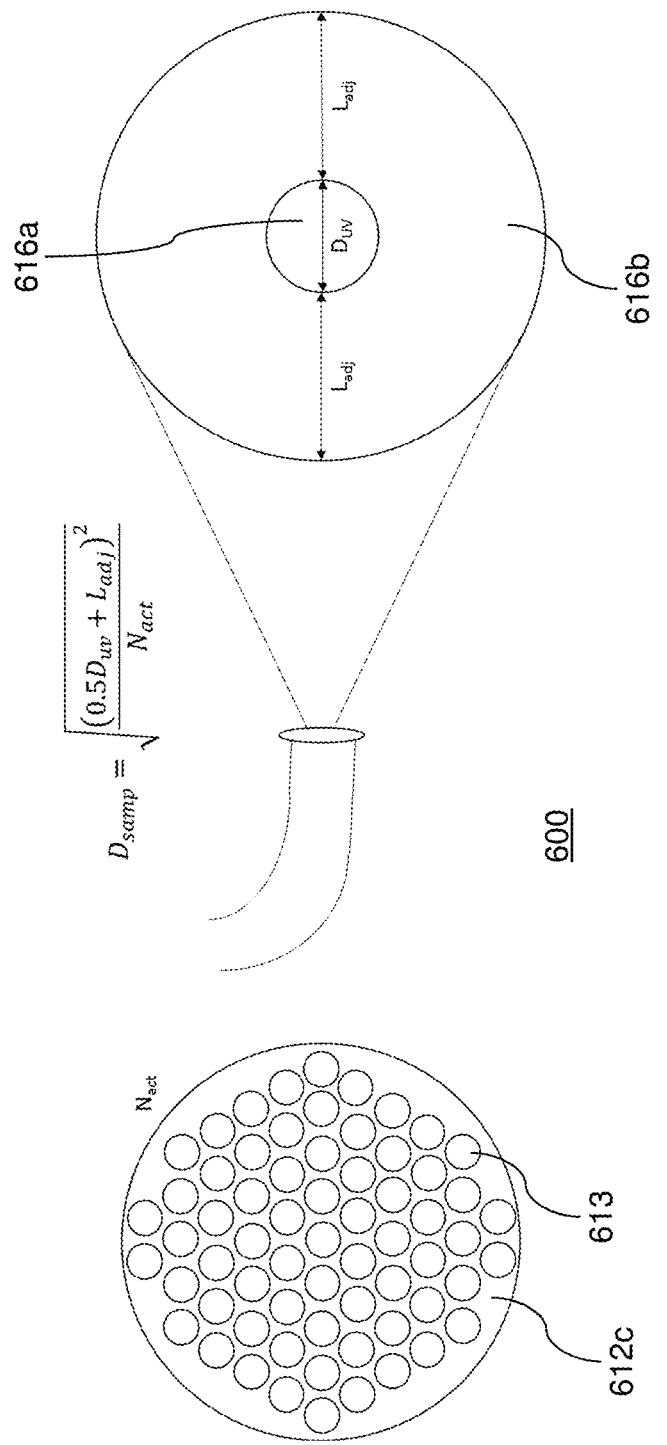
FIG. 6 illustrates an example approach for optimizing a number of fibers in a coherent fiber bundle to project a UV light pattern onto target tissue, according to aspects of the present disclosure.

FIG. 6 illustrates an example approach 600 for optimizing the number of fibers in a coherent fiber bundle 612c. As shown in FIG. 6, an example treatment pattern for a cornea is generated in a circular region 616a having a diameter $D_{UV}$ as well as an adjustment region 616b defined by a length $L_{adj}$. The adjustment region 616b provides a spatial buffer within which the UV light pattern can be shifted to accommodate any eye motion. As described above, this shifting can be achieved with a DMD or an XY scanning system. In an example implementation, $D_{UV}$ may be approximately 10 mm and $L_{adj}$ may be approximately 15 mm, resulting in a total region having a diameter of approximately 40 mm on the cornea. This 40 mm region corresponds to the transmission of UV light from the distal end of a coherent fiber bundle 612c. Fiber bundles typically specify a number of usable fibers 613 that are a central subset of the total number of fibers. The number of these usable fibers 613, also known as "active pixels," is denoted as $N_{act}$. Ideally, the entirety of the UV light pattern fills the entirety of the active pixels, such that each fiber 613 (i.e., pixel) in the coherent fiber bundle 612c samples $1/N_{act}$ of the total UV light pattern. The diameter of the sample relayed by each pixel, $D_{samp}$, is therefore:

$$D_{samp} = \sqrt{\frac{(0.5 D_{uv} + L_{adj})^2}{N_{act}}}$$

Using two example fiber bundles with 17,700 or 87,000 active pixels, with $D_{UV}$ being fixed at 10 mm and $L_{adj}$ being fixed at 15 mm, the diameter of the sample $D_{samp}$ relayed by each pixel is calculated as 150.3 μm or 67.8 μm, respectively. According to research by the inventors associated with the disclosure in U.S. Provisional Patent Application Ser. No. 62/638,621, filed Mar. 5, 2018, the contents of which are incorporated entirely herein by references, it is known that these effective pixel sizes are acceptable for corneal cross-linking treatments. On the other hand, a lower-resolution bundle with 2,000 active pixels provides $D_{samp}$ of 447.2 μm, which may be too large for effective corneal cross-linking in some cases.

Figure 7:
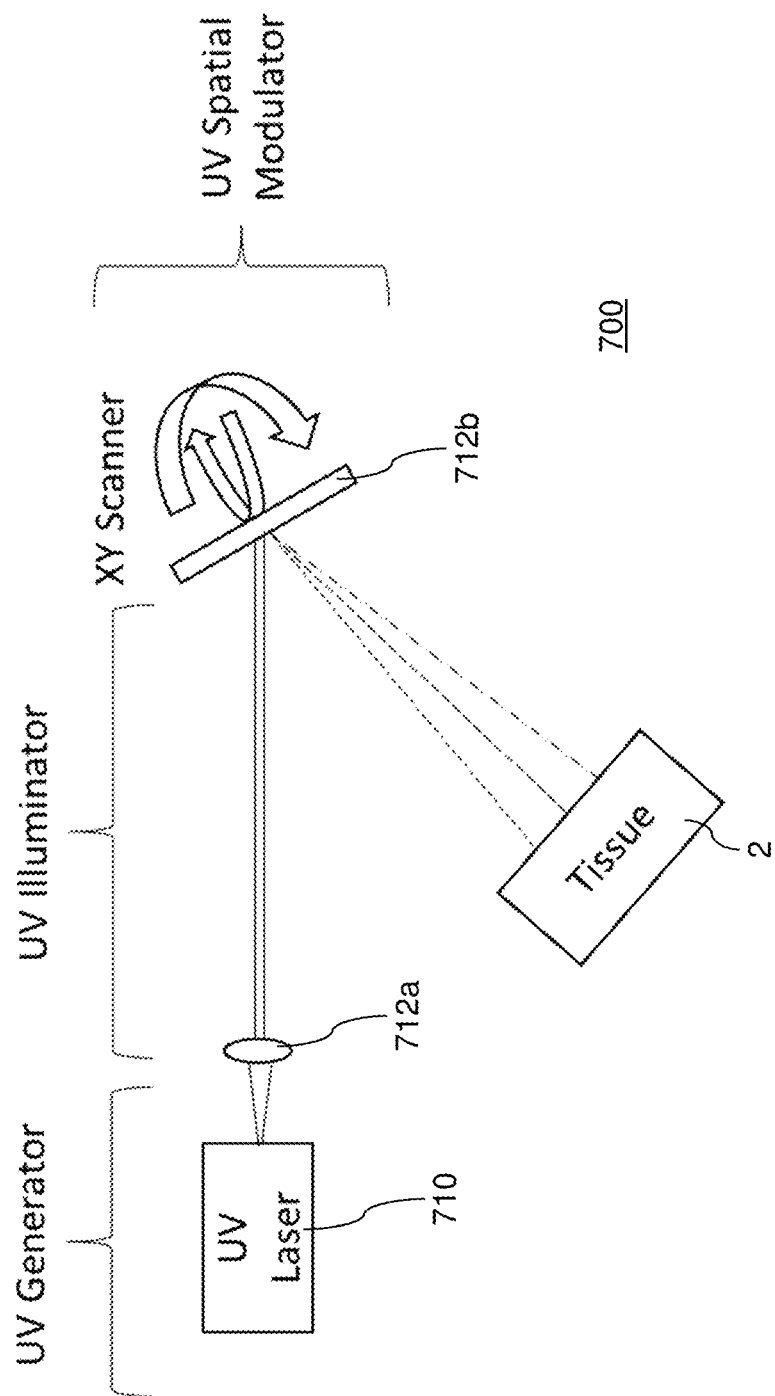
FIG. 7 illustrates an alternative treatment system without any fiber-optic elements, where UV light is generated with a laser source and illuminated onto a XY scanning system, and a resulting UV light scan pattern is projected onto target tissue, according to aspects of the present disclosure.

FIG. 7 illustrates an alternative treatment system 700 that employs a UV laser and a XY scanning system without any fiber-optic elements. The treatment system 700 includes a UV laser source 710 and a lens 712a that collimates the UV laser to a beam with a desired width. The treatment system 700 also includes a XY scanning system 712b. The beam from the lens 712a illuminates the XY scanning system 712b, which directly scans the beam over the cornea 2 according a desired treatment pattern.

In some cases, the Rayleigh range of the beam is sufficiently long that only the lens 712a is needed. For example, at a wavelength of 365 nm and a beam waist of 150 um, the Rayleigh range is 19.4 cm, which provides for a sufficient working distance between the treatment system 700 and the cornea 2.

In other cases, a smaller treatment pattern may be desired. For instance, a spot size of 25 μm or 100 μm may be desired for the treatment pattern. In such cases, the Rayleigh ranges are only 0.5 cm or 8.61 cm, respectively, which would not provide sufficient working distance from the instrument. As such, an alternative lens in place of the lens 712a can be configured to focus the beam from the laser source 710 to produce the desired spot size on the cornea 2, such that the beam is constantly converging from the laser source 710 to the XY scanning system 712b and to the cornea 2. If the laser source 710 pre-collimates the laser beam by nature of its design, a pair of lenses may be employed in place of the lens 712a to first expand the beam and then focus the beam at a desired working distance. Additionally or alternatively, a scan lens may be employed between the XY scanning system 712b and the cornea 2. Use of such a scan lens allows the angular spread of the scan pattern to be converted to a flat scan pattern, as is commonly done in high numerical aperture laser microscopy applications.

Figure 8:
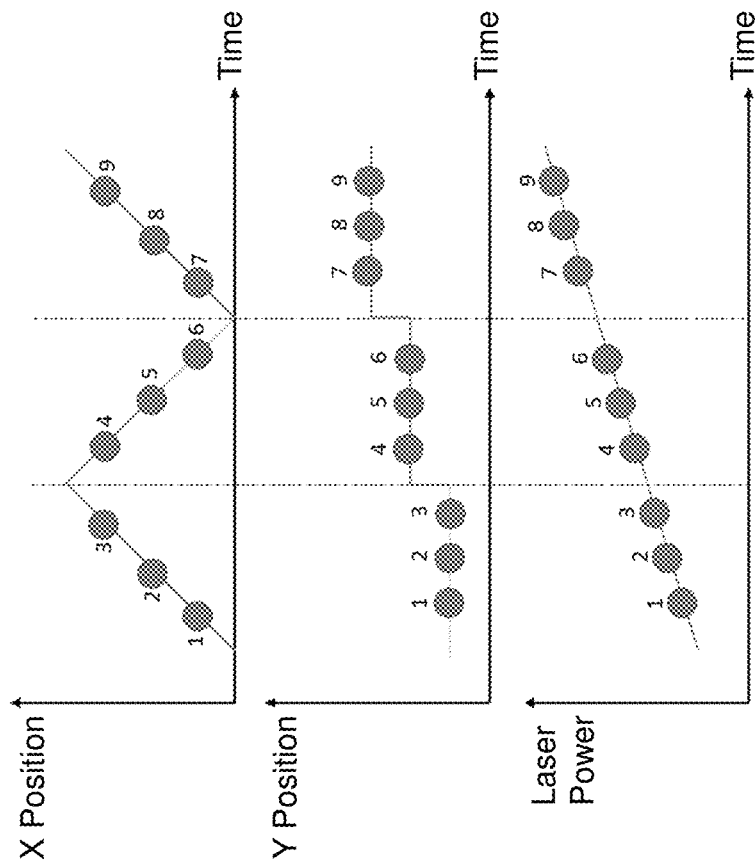
FIG. 8 illustrates an example approach for temporally modulating a spot of UV laser light to spatially adjust doses of UV light applied to target tissue, according to aspects of the present disclosure.
Figure 8:
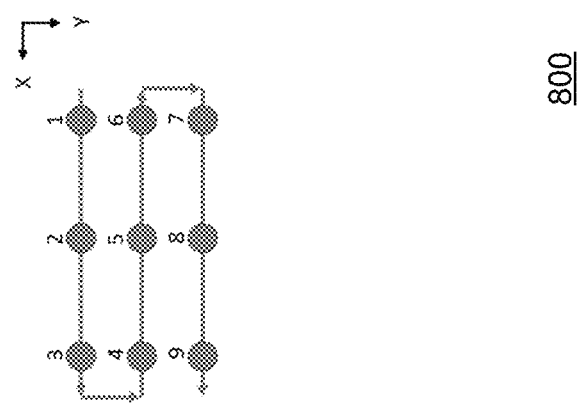

FIG. 8 illustrates an example approach 800 for temporally modulating a UV laser spot to spatially adjust doses of UV light applied to the cornea. The UV laser spot may be generated and projected onto the cornea with an embodiment employing a laser source and a XY scanning system as described above (e.g., the treatment system 500 or 700). Laser output power may be adjusted synchronously with the x- and y-position of the UV laser spot on the cornea. For instance, when the XY scanning system is configured to project a laser spot on a first location on the cornea, the drive current to the laser may be configured at a first level to produce a first output power. Then, when the XY scanning system moves the laser spot to a second location on the cornea, the drive current to the laser may be adjusted to a second level to produce a second output power. Applying a modulated laser drive current that is synchronized to the XY scanning waveforms (e.g., mirror drive waveforms for a galvanometer pair) therefore allows pixel-by-pixel adjustment of UV dose delivered to the cornea. As shown in FIG. 8, an amount of UV laser power applied at each spot location (1-9) is incrementally higher than at the prior spot location. The x- and y-positions are adjusted by application of corresponding drive waveforms to the XY scanning system, as described above. The laser power is adjusted by application of a corresponding current drive waveform to the UV laser source.

Scanning a UV laser spot as illustrated for instance in FIG. 8 may also provide photochemical kinetic advantages due to improved oxygen dynamics. As described above, the presence of oxygen also affects the amount of corneal cross-linking. As the UV laser spot may be stationary or nearly stationary at a given location (x, y) on the cornea for only 10 μs to 100 μs or several milliseconds, and may not return to the same location (x, y) for several milliseconds or several hundred milliseconds or several seconds, oxygen in the column of tissue at the location (x, y) has time to replenish. This may increase the average availability of oxygen in the tissue during cross-linking treatment, which may increase the overall rate and density of crosslink formation.

It may be advantageous to configure the combination of spot size, laser power, and scan speed such that aerobic conditions are always present within the volume of tissue illuminated by the UV laser spot at any point in time. For instance, the scan speed may be selected such that an area on the cornea having the same size as the UV laser spot is transited by the laser in a time T. Then, the laser power may be configured such that oxygen is not fully depleted in the illuminated volume of tissue in the time T, based on the known rate of oxygen consumption during corneal cross-linking as a function of incident laser power. Finally, the overall scan frequency F may be configured such that the same area on the cornea is not illuminated by the UV laser spot again until sufficient amounts of oxygen have rediffused back into the corresponding volume of tissue. In this way, aerobic crosslinking reactions will dominate the overall procedure, increasing the efficiency and density of crosslink formation. Advantageously, this allows aerobic crosslinking at high speeds without the need to deliver supplemental oxygen via gaseous or liquid forms to the cornea. Indeed, the inventors have conducted recent experiments that indicate that this laser-based cross-linking approach may produce as much or more stiffening than existing LED-based approaches.

In contrast to approaches that employ an excimer laser with a wavelength of 193 nm according to a high-intensity pulsed regime to produce a photoablative effect on corneal tissue, the UV laser spot employed in the embodiments above is configured to avoid a photoablative effect. For instance, the laser may have a wavelength of approximately 365 nm and may be provided in a continuous-wave or amplitude-modulated mode but not a pulsed mode, and the incident power may be significantly below the photoablation threshold.

Figure 9:
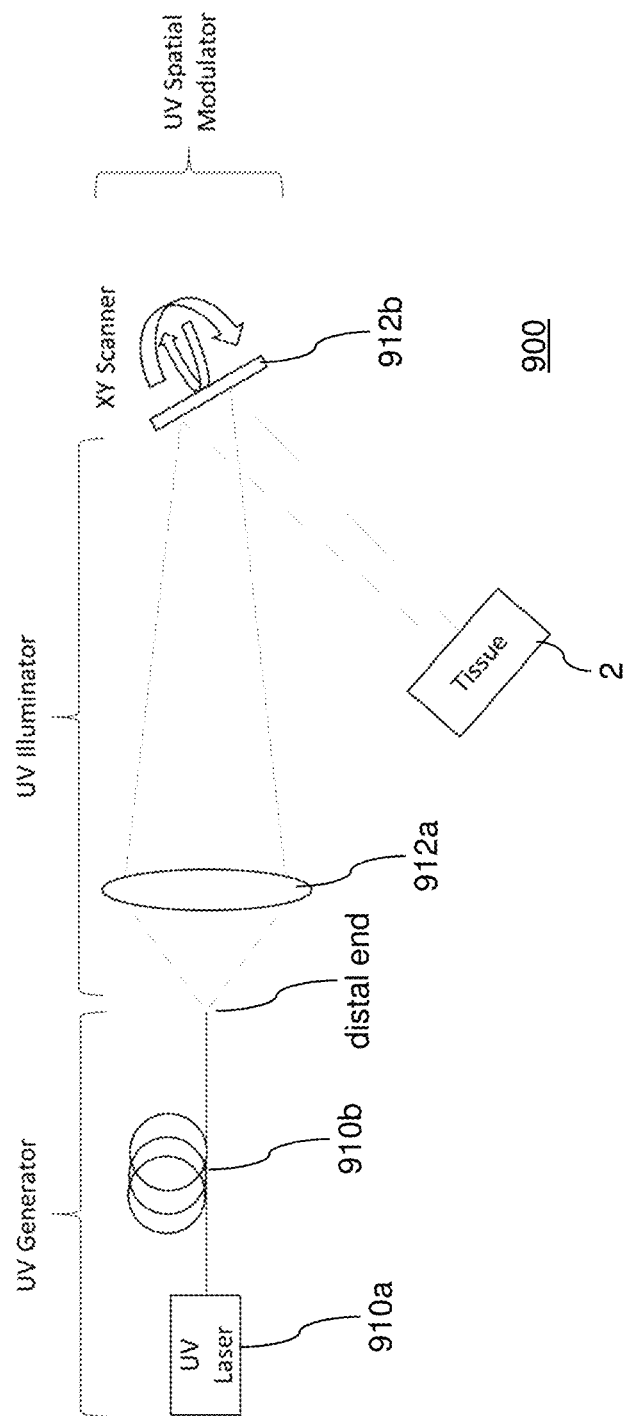
FIG. 9 illustrates another example treatment system, where UV light is generated with a laser source and illuminated onto a XY scanning system, and a resulting UV light scan pattern is projected onto target tissue, according to aspects of the present disclosure.

FIG. 9 illustrates another example treatment system 900 that employs a UV laser and a XY scanning system. The treatment system 900 includes a UV laser source 910a and a lens 912a. In contrast to the treatment system 700 described above, the treatment system includes a single-mode or multi-mode optical fiber 910b which routes the UV light generated by the UV laser source 910a to the lens 912a. The optical fiber 910b provides the additional advantage of allowing the UV laser source 910a to be positioned anywhere in the system, e.g., further reducing the complexity, size, weight, and cost of the XYZ motion stage as described above. The light diverging from a distal end of the optical fiber 910b is focused with the lens 912a. In particular, the lens 912a is configured to provide a beam that produces a desired focal spot size on a cornea 2 at a desired distance from the lens 912a. As shown in FIG. 9, only the single lens 912a is employed, but other embodiments may employ additional lenses. The beam from the lens 912a may constantly converge as it travels from the lens 912a to the cornea 2. The treatment system 900 also includes an XY scanning system 912b, which is positioned between the lens 912a and the cornea 2. The beam from the lens 912a illuminates the XY scanning system 912b, which directly scans the beam over the cornea 2 according a desired treatment pattern as described above.

Figure 10:
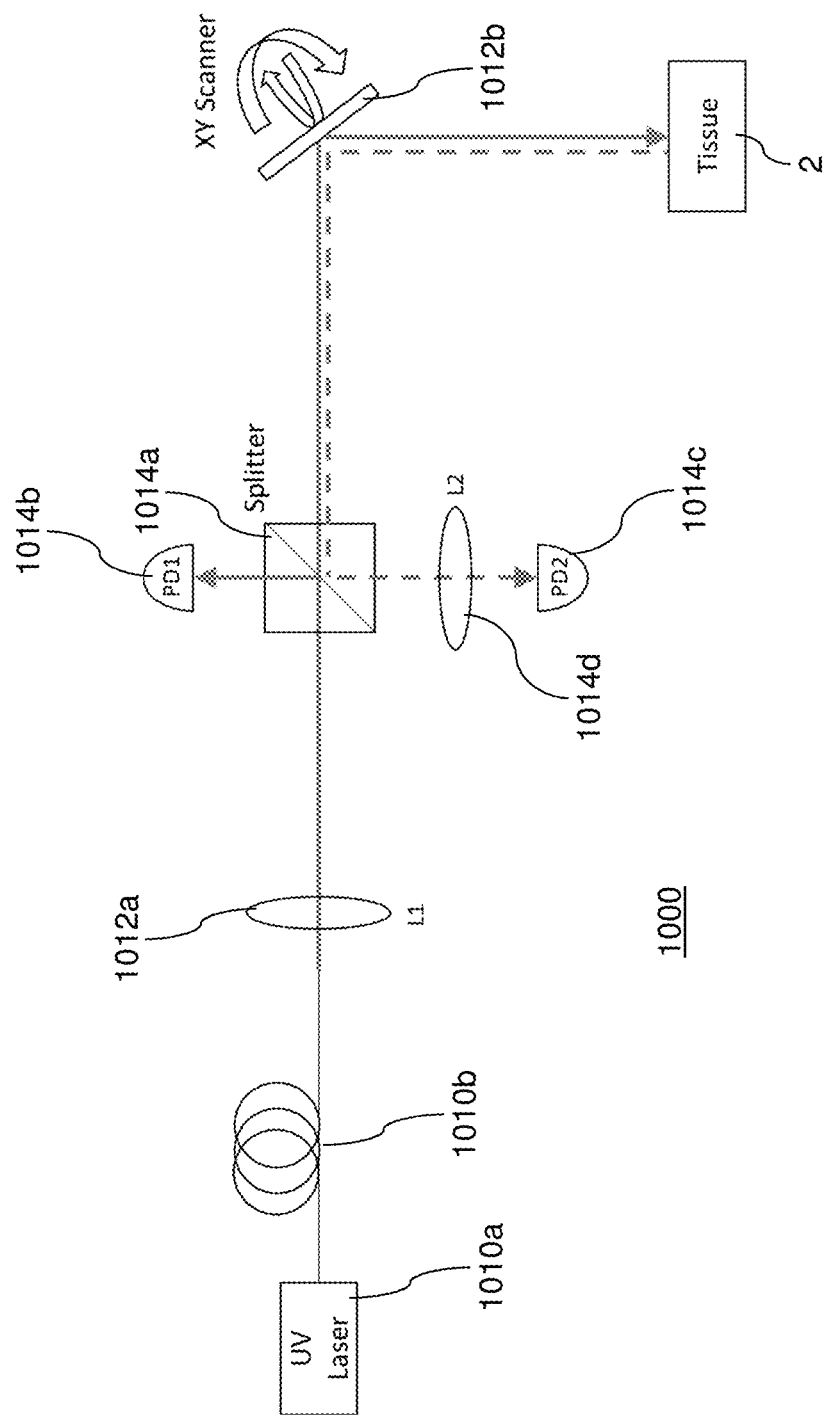
FIG. 10 illustrates a further example treatment system which modifies the treatment system of FIG. 9 to incorporate diagnostic features, according to aspects of the present disclosure.

FIG. 10 illustrates a further example treatment system 1000 which modifies the treatment system 900 described above to incorporate diagnostic features. Similar to the treatment system 900, the treatment system 1000 includes a UV laser source 1010a and a first lens 1012a. The treatment system 1000 also includes a single-mode or multi-mode optical fiber 1010b which routes the UV light generated by the UV laser source 1010a to the first lens 1012a. As FIG. 10 shows, the treatment system 1000 also includes a beamsplitter 1014a, which may be a dichroic beamsplitter. The beamsplitter 1014a is positioned to receive a beam of the UV light transmitted by the first lens 1012a. The beamsplitter 1014a is configured to transmit a large fraction (e.g., greater than 90%) of light below a selected wavelength close to the wavelength of the UV laser (e.g., less than 390 nm) and to reflect a large fraction of light above that selected wavelength. The treatment system 1000 includes a first photodiode 1014b that can be positioned to receive a first output (i.e., the reflected UV light) from the beamsplitter 1014a. In particular, the first photodiode 1014b may be employed to monitor a portion (e.g., approximately 10%) of the UV power being delivered to the tissue 2. The treatment system 1000 also includes an XY scanning system 1012b, which is positioned between the beamsplitter 1014a and the cornea 2. The light transmitted by the beamsplitter 1014a illuminates the XY scanning system 1012b, which directly scans the beam over the cornea 2 according a desired treatment pattern.

As described further below, the cornea 2 may emit fluorescent light signals at different points of a cross-linking treatment. The fluorescent light signals can be evaluated to assess aspects of the cross-linking treatment. The fluorescent light travels to the XY scanning system 1012b and the beamsplitter 1014a (shown as a dotted line in FIG. 10). Because the fluorescent light has a wavelength greater than the selected wavelength, the beamsplitter 1014a also reflects the fluorescent light (rather than transmitting the fluorescent light). As such, the treatment system 1000 includes a second photodiode 1014c (or alternatively, a spectrometer or camera) that can be positioned to receive a second output (i.e., the fluorescent light) from the beamsplitter 1014a. The second photodiode 1014c may be employed to monitor fluorescent light that is emitted by the cornea 2 before, during, and/or after cross-linking activity is generated in the cornea 2. The treatment system 1000 may include a second lens 1014d to improve coupling efficiency of the fluorescent light into the second photodiode 1014c.

Figure 11:
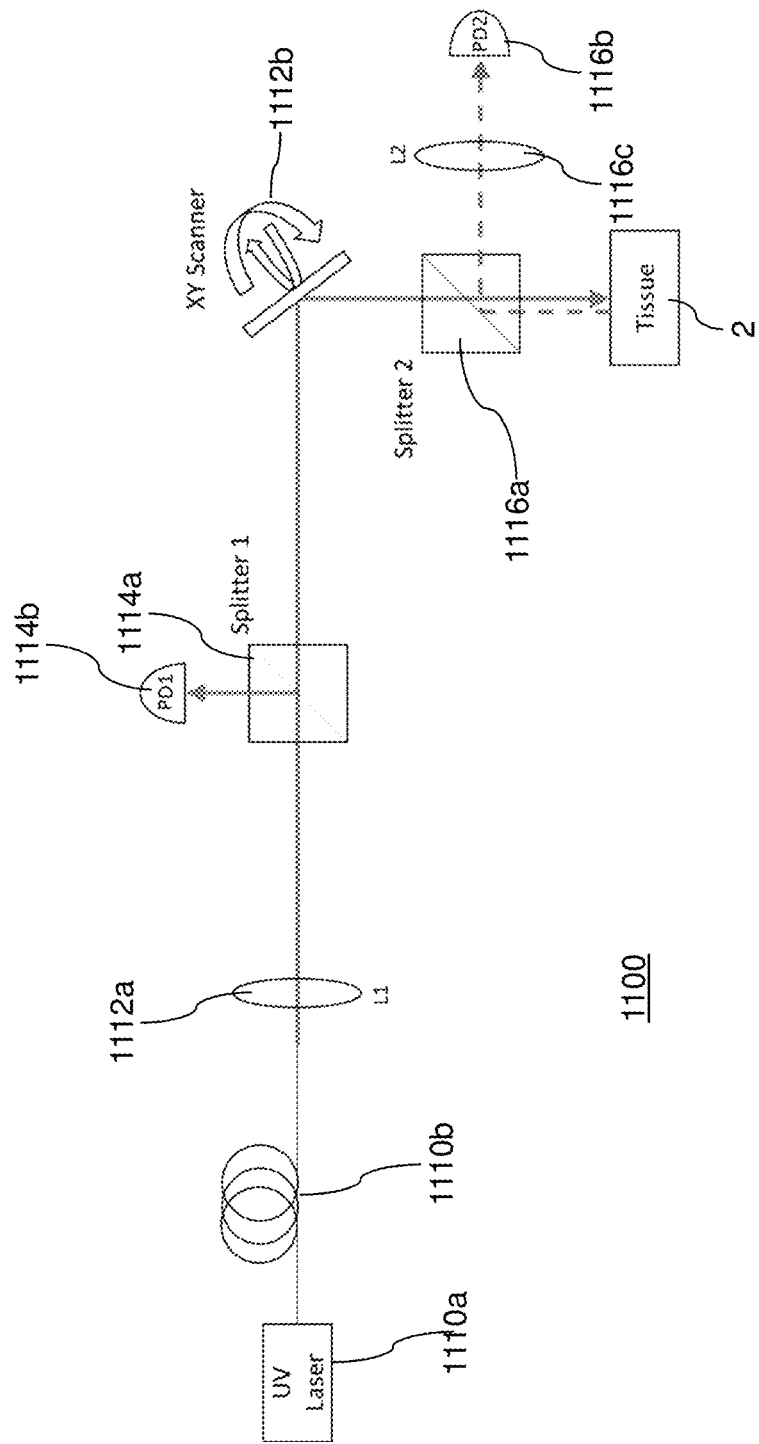
FIG. 11 illustrates yet another treatment system that employs diagnostic features, according to aspects of the present disclosure.

FIG. 11 illustrates yet another treatment system 1100 which also incorporates diagnostic features. Similar to the treatment system 1000, the treatment system 1100 includes a UV laser source 1110a and a first lens 1112a. The treatment system 1100 also includes a single-mode or multi-mode optical fiber 1110b which routes the UV light generated by the UV laser source 1110a to the first lens 1112a. The treatment system 1100 includes a first beamsplitter 1114a (e.g., a dichroic beamsplitter) and a first photodiode 1114b. The first beamsplitter 1114a is positioned to receive a beam of the UV light transmitted by the first lens 1112a. The first beamsplitter 1114a is configured to transmit a large fraction of light below a selected wavelength close to the wavelength of the UV laser and to reflect a large fraction of light above that selected wavelength. The first photodiode 1114b receives the reflected UV light from the first beamsplitter 1114a and can be employed to monitor a portion of the UV power being delivered to the tissue 2. The treatment system 1100 also includes a XY scanning system 1112b. The light transmitted by the first beamsplitter 1114a illuminates the XY scanning system 1112b, which directly scans the beam over the cornea 2 according a desired treatment pattern.

In contrast to the treatment system 1000, the treatment system 1100 also includes a second beamsplitter 1116a, which may be a dichroic beamsplitter. The second beamsplitter 1116a is positioned between the XY scanning system 1112b and the cornea 2. The second beamsplitter 1116a is configured to transmit the beam from the XY scanning system 1112b to the cornea 2 and allow the beam to be scanned over the cornea 2 as desired. The cornea 2 may emit a fluorescent light, which can be evaluated to assess aspects of the cross-linking treatment. This fluorescent light travels to the second beamsplitter 1116a (shown as a dotted line in FIG. 11). The second beamsplitter 1116a is configured to reflect the fluorescent light (rather than transmit the fluorescent light to the XY scanning system 1112b). The treatment system 1100 includes a second photodiode 1116b (or alternatively, a spectrometer or camera) that can be positioned to receive the fluorescent light from the second beamsplitter 1116a. The second photodiode 1116b may be employed to monitor fluorescent light that is emitted by the cornea 2 before, during, and/or after cross-linking activity is generated in the cornea 2. The treatment system 1100 may include a second lens 1116c to improve coupling efficiency of the fluorescent light into the second photodiode 1116b.

Advantageously, the position of the second beamsplitter 1116a closer to the tissue 2 (i.e., between the XY scanning system 1112b and the tissue 2) improves the efficiency of fluorescent light collection by the second photodiode 1116b. This arrangement also allows a larger optical aperture to be used to collect the fluorescent light because the fluorescent light does not first travel through the XY scanning system 1112b. In the treatment system 1000 described above, the size of the mirrors of the XY scanning system 1012b may be only several mm in diameter and can thus constrain subsequent collection of the fluorescent light at the beamsplitter 1014a.

The embodiments above may also include additional elements, such as cameras and fixation light sources, which may assist with visualization of the eye for alignment and tracking purposes. Such elements may be arranged coaxially with the treatment beam by employing additional beamsplitters. Alternatively, these elements may also be arranged in an off-axis manner by mounting them outside of the path of the UV laser beam. Alternatively, dichroic beamsplitters may be replaced by other optical elements, such as trichroic beamsplitters, prisms, or diffraction gratings, which allow multiple wavelength bands of fluorescent light from the tissue to be spatially separated and captured by multiple photodiodes. This has the additional advantage of allowing multiple fluorescent signals to be simultaneously evaluated before, during, or after cross-linking, such as fluorescent signals from collagen, nicotinamide adenine dinucleotide (NADH), or other biological materials in addition to fluorescent signals from the cross-linking agent.

Figure 12A:
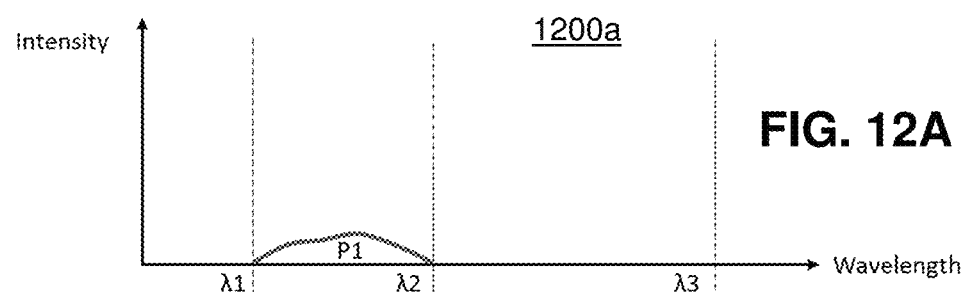
FIG. 12A illustrates an example graph of detected fluorescence signals prior to administration of riboflavin in a cross-linking treatment, according to aspects of the present disclosure.
Figure 12B:
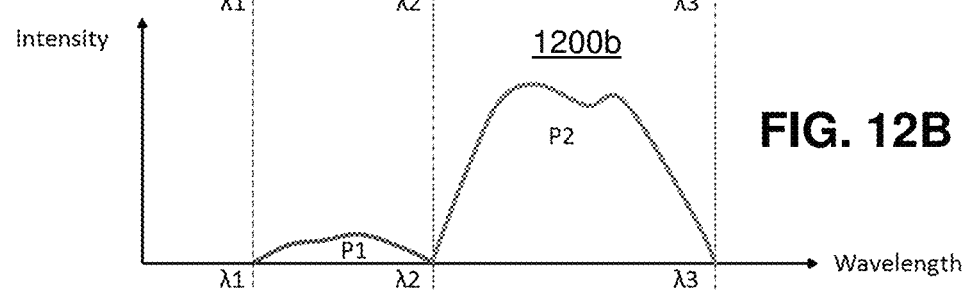
FIG. 12B illustrates an example graph of detected fluorescence signals after administration of riboflavin in a cross-linking treatment, according to aspects of the present disclosure.
Figure 12C:
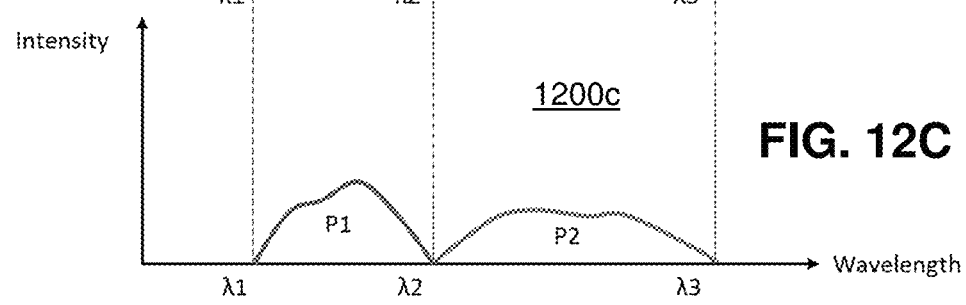
FIG. 12C illustrates an example graph of detected fluorescence signals during application of UV light in a cross-linking treatment, according to aspects of the present disclosure.

As the example graphs of FIGS. 12A-C illustrate, detected fluorescence signals may change over time during a cross-linking treatment. Prior to administration of riboflavin as shown by graph 1200a in FIG. 12A, corneal tissue auto-fluorescence, for instance from NADH or collagen, may be present at a low level in a first wavelength band $\lambda 1$-$\lambda 2$. After administration of riboflavin as shown by graph 1200b in FIG. 12B, exogenous fluorescence may appear at a high level in a second wavelength band $\lambda 2$-$\lambda 3$ while the auto-fluorescence in the first wavelength band $\lambda 1$-$\lambda 2$ remains stable. During application of UV light as shown by graph 1200c in FIG. 12C, auto-fluorescence in the first wavelength band $\lambda 1$-$\lambda 2$ may increase, while the exogenous fluorescence in the second wavelength band $\lambda 2$-$\lambda 3$ from the riboflavin may decrease. At the same time, the exogenous fluorescence from products, such as lumichrome and lumiflavin, resulting from the degradation of the riboflavin may increase. By collecting fluorescent light, embodiments, such as the treatment systems 1000, 1100, can monitor tissue uptake of riboflavin prior to cross-linking and the progression of cross-linking during exposure to UV light. The fluorescent light signals may be resolved spectrally by use of a spectrometer or may be integrated over discrete wavelength bands (shown as signal levels P1 and P2 in FIGS. 12A-C) by use of appropriate optical filters and photodiodes.

Figure 13:
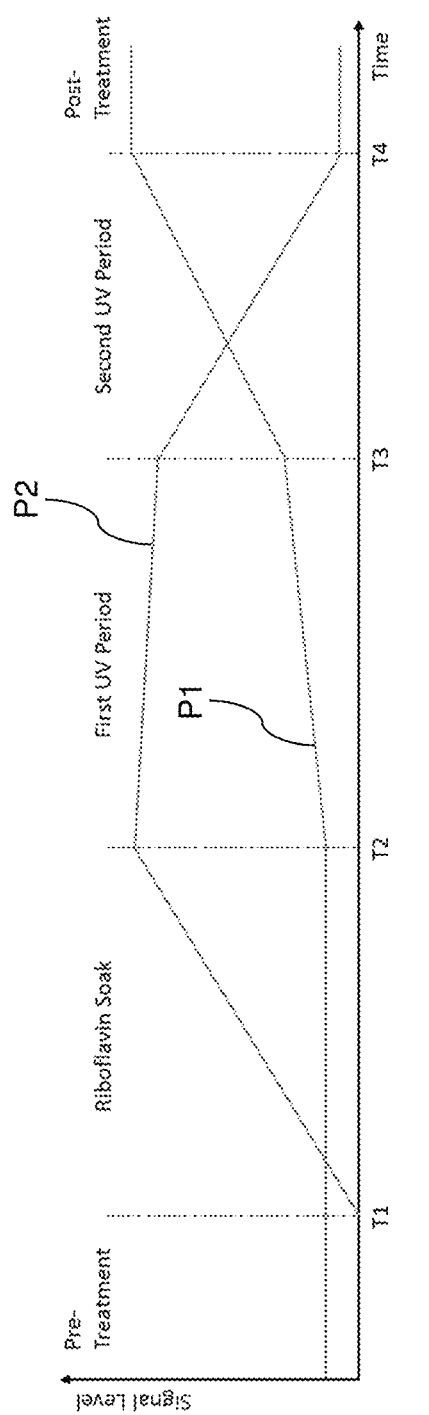
FIG. 13 illustrates an example graph of signal levels associated with auto-fluorescence and exogenous fluorescence during different periods in a cross-linking treatment, according to aspects of the present disclosure.

FIG. 13 illustrates an example graph 1300 of signal levels associated with the auto-fluorescence in the first wavelength band $\lambda 1$-$\lambda 2$ (identified as P1) and the exogenous fluorescence in the second wavelength band $\lambda 2$-$\lambda 3$ (identified as P2), during different periods in a cross-linking treatment. Real time monitoring of signal levels P1 and P2 may be used to guide the cross-linking treatment. During a riboflavin soak period (shown as T1-T2 in FIG. 13), signal level P2 may be monitored to ensure that sufficient riboflavin is present prior to photoactivation with UV light. For instance, a practitioner may be prompted to extend the riboflavin soak period if signal level P2 has not reached a predetermined threshold. During a first photoactivation period (shown as T2-T3 in FIG. 13), photoactivation of riboflavin may cause signal level P2 to decrease while cross-link formation causes signal level P1 to increase. Either by direct or ratio-metric measurement of signal level P1 and signal level P2 over this time period, the rate of consumption of riboflavin and the rate of production of cross-linking sites can be evaluated. Such evaluation of the rate of consumption of riboflavin, the rate of production of cross-linking sites, and/or the relative ratio of these two rates can be used to assess the efficiency of the cross-linking treatment. If needed, photoactivation parameters (i.e., aspects of UV light application) can be adjusted in real time to ensure that sufficient density of cross-links are formed before the treatment is ended. For instance, irradiance may be decreased to improve efficiency or total dose may be increased in real time. During a second photoactivation period (shown as T3-T4 in FIG. 13), the signal levels P1 and P2 may be monitored further to ensure that desired fluorescent light signal endpoints are reached.

In some embodiments, the use of the XY scanning systems allows measurement of any spatial variation in the relative rates of riboflavin consumption and cross-linking production. Additionally, the XY scanning systems also allow spatial adjustment of photoactivation parameters in real time to achieve more optimal treatments. In some cases, the relative ratio of signal levels P1 and P2 may need to be calibrated to account for the fact that riboflavin in collagen may absorb a portion of the auto-fluorescence associated with the signal level P1. Such calibration may involve scaling the measured magnitude of the signal level P1. This scaling may depend on the magnitude of the signal level P1 and can occur in real time.

By measuring the auto-fluorescence prior to the start of the cross-linking treatment as a baseline (before application of the riboflavin and photoactivation) and monitoring the signal levels P1 and P2 in real time during the cross-linking treatment, a practitioner can determine when substantially all the riboflavin has been consumed and/or when more optimal cross-link densities have been achieved. Real time monitoring can therefore be used to determine when the cross-linking treatment should be stopped, e.g., when the desired treatment results have been achieved, or when the cross-linking treatment should be paused, e.g., when the riboflavin has been exhausted before the desired treatment results have been achieved. In the latter case, the cross-linking treatment can be resumed following the administration of more riboflavin.

Additionally, changes in peak intensity for the auto-fluorescence (signal level P1)/the rate of cross-linking production may be evaluated to assess local changes in corneal stiffness. Such assessment of changes in corneal stiffness may be considered in combination with a corneal biomechanical model to assess changes in corneal shape and/or a vision model to assess changes in patient vision.

Accordingly, monitoring of the signal levels P1 and P2 can be used to determine locally varying rates of riboflavin consumption and cross-link formation. These rates may vary from eye to eye or may vary locally across the cornea. Real time monitoring of these rates during treatment allows treatment parameters to be adjusted to optimize treatment results. Real time monitoring allows a practitioner to determine if the concentration of riboflavin has been exhausted or to determine when the cross-linking treatment should be stopped. Generally, treatment parameters can be adjusted to control: (i) the rate of cross linking production according to a prescribed level; (ii) changes in corneal stiffness according to a prescribed level (which may involve correlation between the rate of cross-link formation and increases in corneal stiffness); (iii) changes in corneal shape according to a prescribed treatment result (which may involve use of a corneal biomechanical model to calculate corneal shape changes induced by volumetric changes in cross-link densities); or (iv) changes in vision according to a prescribed treatment result (which may involve use of a corneal biomechanical model and a vision model to calculate changes in patient vision induced by volumetric changes in cross-link densities).

Furthermore, pre-treatment signal levels P1 (auto-fluorescence) may be correlated with rates of cross-linking production (cross-linking efficiency). As such, treatment parameters can be titrated prior to the start of cross-linking treatment based on a pre-treatment measurement of collagen auto-fluorescence.

Figure 14B:
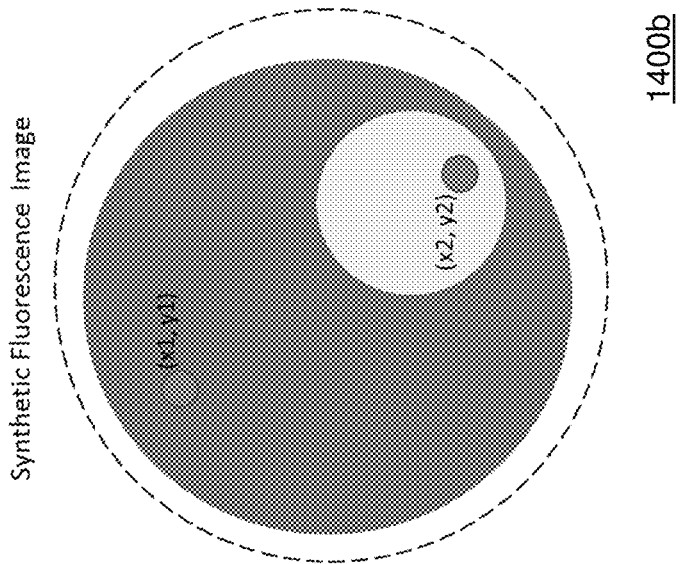
FIG. 14B illustrates an example a synthetic fluorescence image associated with the example scan pattern of FIG. 14A, according to aspects of the present disclosure.
Figure 14A:
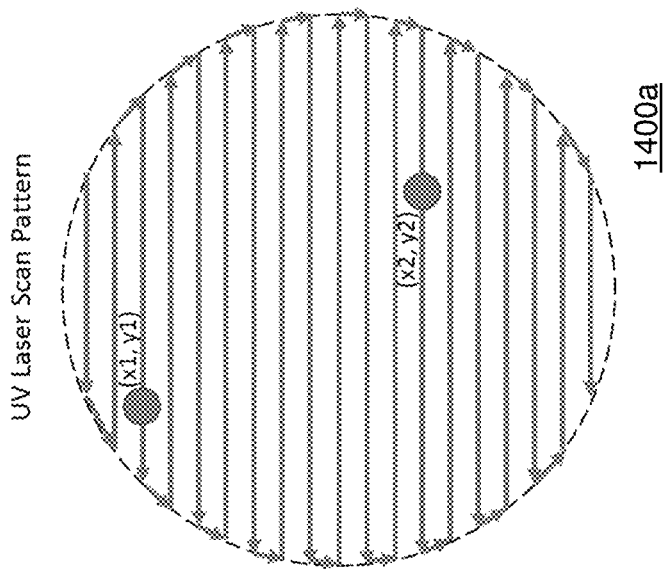
FIG. 14A illustrates an example scan pattern that can be achieved by an XY scanning system, according to aspects of the present disclosure.

FIG. 14A illustrates an example scan pattern 1400a that can be achieved by an XY scanning system as described above. Since the (x, y) coordinates of the spot of UV light on the cornea are known at each point in time, a synthetic fluorescence image 1400b as shown in FIG. 14B can be generated and presented to the practitioner. A greyscale or color value at each (x, y) coordinate in the synthetic image 1400b may correspond to the signal levels P1 and P2, or the ratio of the signal level P1 to the signal level P2. For instance, the signal level P1 may be higher at coordinate (x1, y1) than the signal level P2 at coordinate (x2, y2). By presenting the synthetic fluorescence image 1400b during the riboflavin soak period, the practitioner can understand the spatial distribution of the drug prior to UV photoactivation. By presenting the synthetic fluorescence image 1400b during UV photoactivation, the practitioner can understand the spatial distribution of cross-link formation in order to make subsequent decisions about patient treatment, for example identifying the need for additional treatments.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A system for treating an eye, comprising:
   a light source configured to provide photoactivating light that photoactivates a cross-linking agent applied to a cornea;
   one or more optical elements configured to receive the photoactivating light and produce a beam that defines a spot of the photoactivating light;
   a scanning system configured to receive the beam of the photoactivating light and to scan the spot of the photoactivating light along a first axis and a second axis to form a scan pattern defined by a plurality of treatment zones on the cornea to generate cross-linking activity, the plurality of treatment zones including at least a first treatment zone and a second treatment zone, the first treatment zone providing a first dose of the photoactivating light, the second treatment zone providing a second dose of the photoactivating light, the first dose being greater than the second dose; and a moveable optical fiber bundle configured to receive the scan pattern from the scanning system and to transmit the scan pattern to the cornea, the moveable optical fiber bundle being contained within a circular region having an adjustment region configured to provide a spatial buffer.

2. The system of claim 1, wherein the scanning system includes a galvanometer pair, the galvanometer pair including a first mirror configured to scan the spot of the photoactivating light along the first axis and a second mirror configured to scan the spot of the photoactivating light along the second axis.

3. The system of claim 1, wherein at least one of the light source or the scanning system is operable to spatially adjust doses of the photoactivating light delivered in respective portions of the scan pattern.

4. The system of claim 1, wherein the scanning system is configured to scan the spot of the photoactivating light along the first axis according to a first adjustable speed and to scan the spot of the photoactivating light along the second axis according to a second adjustable speed, the first adjustable speed and the second adjustable speed determining a dwell time for the spot of the photoactivating light over a portion of the scan pattern and determining a dose of the photoactivating light delivered for cross-linking activity in the portion of the scan pattern.

5. The system of claim 1, wherein the light source is operable to adjust a power associated with the beam as the scanning system scans the spot of the photoactivating light over portions of the scan pattern, the portions of the scan pattern receiving doses of the photoactivating light based on the power associated with the beam.

6. The system of claim 1, wherein the light source is operable to adjust a power associated with the beam, the one or more optical elements is operable to adjust a size of the spot of the photoactivating light produced by the beam, and the scanning system is operable to adjust a speed of the spot of the photoactivating light over portions of the scan pattern.

7. The system of claim 6, wherein at least one of the power associated with the beam, the size of the spot of the photoactivating light, and the speed of the spot of the photoactivating light is adjusted to aerobic conditions in the cornea for the cross-linking activity.

8. The system of claim 1, further comprising a photodiode configured to receive a portion of the beam of the photoactivating light to monitor a power of the beam of the photoactivating light.

9. The system of claim 1, further comprising a photodiode configured to receive fluorescent light from the cornea to monitor the cross-linking activity.

10. The system of claim 9, wherein the photodiode receives fluorescent light from a portion of the scan pattern corresponding to the position of the spot of the photoactivating light along the first axis and the second axis.

11. The system of claim 9, wherein the fluorescent light includes auto-fluorescence from corneal tissue and exogenous fluorescence resulting from a degradation of the cross-linking agent, and the system further comprises a controller configured to:

receive, from the photodiode, a first signal corresponding to the auto-fluorescence and a second signal corresponding to the exogenous fluorescence; and determine spatial variations in relative rates of cross-linking consumption and cross-linking activity in the cornea based on changes in the first signal and the second signal provided by the photodiode as the spot of photoactivating light is scanned over the scan pattern.

12. The system of claim 11, wherein, in response to the spatial variations, the light source is operable to adjust a power associated with the beam, the one or more optical elements is operable to adjust a size of the spot of the photoactivating light produced by the beam, and/or the scanning system is operable to adjust a speed of the spot of the photoactivating light over portions of the scan pattern.

13. The system of claim 1, further comprising one or more beamsplitters configured to direct a portion of the beam of the photoactivating light to a first photodiode to monitor a power of the beam of the photoactivating light and to direct fluorescent light from the cornea to a second photodiode to monitor the cross-linking activity.

14. The system of claim 13, wherein the one or more beamsplitter includes a first beamsplitter configured to direct the portion of the beam of the photoactivating light to the first photodiode and a second beamsplitter configured to direct the fluorescent light from the cornea to the second photodiode.

15. A system for treating an eye, comprising:
a light source configured to provide photoactivating light that photoactivates a cross-linking agent applied to a cornea;

one or more optical elements configured to receive the photoactivating light and produce a pattern of photoactivating light defined by a plurality of treatment zones, the plurality of treatment zones including at least a first treatment zone and a second treatment zone, the first treatment zone providing a first dose of the photoactivating light, the second treatment zone providing a second dose of the photoactivating light, the first dose being greater than the second dose; and a moveable fiber-optic element configured to receive the pattern of photoactivating light from the one or more optical elements and transmit the pattern of photoactivating light to the cornea to generate cross-linking activity, the moveable fiber-optic element being contained within a circular region having an adjustment region configured to provide a spatial buffer.

16. The system of claim 15, wherein the one or more optical elements includes a digital micro-mirror device (DMD).

17. The system of claim 15, wherein the one or more optical elements includes a galvanometer pair, the galvanometer pair including a first mirror configured to scan a spot of the photoactivating light along a first axis and a second mirror configured to scan the spot of the photoactivating light along a second axis.

18. The system of claim 15, further comprising an additional fiber-optic element configured to receive the photoactivating light from the light source and transmit the photoactivating light to the one or more optical elements.

19. The system of claim 15, further comprising a motion stage coupled to the fiber-optic element and configured to move a distal end of the fiber-optic element to the cornea, the pattern of photoactivating light is delivered from the distal end to the cornea.

* * * * *